US006828151B2

(12) United States Patent
Borchers et al.

(10) Patent No.: US 6,828,151 B2
(45) Date of Patent: Dec. 7, 2004

(54) ANTISENSE MODULATION OF HEMATOPOIETIC CELL PROTEIN TYROSINE KINASE EXPRESSION

(75) Inventors: Alexander H. Borchers, Encinitas, CA (US); Kenneth W. Dobie, Del Mar, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 6 days.

(21) Appl. No.: 10/007,010

(22) Filed: Dec. 4, 2001

(65) Prior Publication Data

US 2003/0125275 A1 Jul. 3, 2003

(51) Int. Cl.[7] .......................... C12Q 1/68; C12N 15/88; C12P 19/34; C07H 21/02; C07H 21/04
(52) U.S. Cl. ......................... 435/458; 435/6; 435/91.1; 435/91.31; 536/23.1; 536/24.5
(58) Field of Search ....................... 435/6, 91.1, 91.31, 435/458, 455; 536/23.1, 24.5, 25.3; 514/44

(56) References Cited

U.S. PATENT DOCUMENTS 5,877,309 A * 3/1999 McKay et al. ............. 536/24.5

OTHER PUBLICATIONS

Karen Pihl–Carey, The Daily Biotechnology Newspaper, vol. 10, No. 239, pp. 1–2.*
Andrea D. Branch, TIBS Feb. 23, 1998, pp. 45–50.*
Giorgio Palu' et al., Journal of Biotechnology, 68 (1999) pp. 1–13.*
Sudhir Agrawal et al., Molecular Medicine Today, Feb. 2000, vol. 6, pp. 72–81.*
Traian V. Chirila et al., Biomaterials 23 (2002) pp. 321–342.*
Natalie Milner et al., Nature Biotechnology, vol. 15, Jun. 1997, pp. 537–541.*
Stanley T. Crooke, pp. 1–50.*
Ingo Tamm et al., The Lancet, vol. 358, Aug. 11, 2001, pp. 489–497.*
Brown et al., *Regulation, substrates and functions of src*, Biochim. Biophys. Acta., 1996, 1287:121–149.
Cartledge et al., *Generation and characterization of monoclonal antibodies to the Src–family kinase Hck*, Hybridoma, 2000, 19:323–330.
Choi et al., *Role of Hck in the pathogenesis of encephalomyocarditis virus–induced diabetes in mice*, J. Virol., 2001, 75:1949–1957.
English et al., *Hck tyrosine kinase activity modulates tumor necrosis factor production by murine macrophages*, J. Exp. Med., 1993, 178:1017–1022.
English et al., *Bacterial LPS and IFN–.gamma. trigger the tyrosine phosphorylation of vav in macrophages: evidence for involvement of the hck tyrosine kinase*, J. Leukocyte Biol., 1997, 62:859–864.

Lichtenberg et al., *Human protein–tyrosine kinase gene HCK: expression and structural analysis of the promoter region*, Oncogene, 1992, 7:849–858.
Lionberger et al., *Transformation of myeloid leukemia cells to cytokine independence by Bcr–Abl is suppressed by kinase–defective Hck*, J. Biol. Chem., 2000, 275:18581–18585.
Lowell et al., *Resistance to endotoxic shock and reduced neutrophil migration in mice deficient for the Src–family kinases Hck and Fgr*, Proc. Natl. Acad. Sci. U. S. A., 1998, 95:7580–7584.
Mocsai et al., *Adhesion–dependent degranulation of neutrophils requires the Src family kinases Fgr and Hck*, J. Immunol., 1999, 162:1120–1126.
Quintrell et al., *Identification of a human gene (HCK) that encodes a protein–tyrosine kinase and is expressed in hemopoietic cells*, Mol. Cell Biol., 1987, 7:2267–2275.
Robbins et al., *Myristoylation and differential palmitoylation of the HCK protein–tyrosine kinases govern their attachment to membranes and association with caveolae*, Mol. Cell Biol., 1995, 15:3507–3515.
Schindler et al., *Crystal structure of HcK in complex with a Src family–selective tyrosine kinase inhibitor*, Mol. Cell, 1999, 3:639–648.
Showalter et al., *Small molecule inhibitors of the platelet–derived growth factor receptor, the fibroblast growth factor receptor, and Src family tyrosine kinases*, Pharmacol. Ther., 1997, 76:55–71.
Taguchi et al., *Characteristic expression of Hck in human B–cell precursors*, Exp. Hematol. (N. Y.), 2000, 28:55–64.
Tokunaga et al., *Inhibition of human immunodeficiency virus type 1 virion entry by dominant–negative Hck*, J. Virol., 1998, 72:6257–6259.
Wei et al., *Critical role of Lyn kinase in inhibition of neutrophil apoptosis by granulocyte–macrophage colony-stimulating factor*, J. Immunol., 1996, 157:5155–5162.
Ziegler et al., *Novel protein–tyrosine kinase gene (hck) preferentially expressed in cells of hematopoietic origin*, Mol. Cell Biol., 1987, 7:2276–2285.

* cited by examiner

*Primary Examiner*—Ram R. Shukla
*Assistant Examiner*—Jane Zara
(74) *Attorney, Agent, or Firm*—Licata & Tyrrell P.C.

(57) ABSTRACT

Antisense compounds, compositions and methods are provided for modulating the expression of hematopoietic cell protein tyrosine kinase. The compositions comprise antisense compounds, particularly antisense oligonucleotides, targeted to nucleic acids encoding hematopoietic cell protein tyrosine kinase. Methods of using these compounds for modulation of hematopoietic cell protein tyrosine kinase expression and for treatment of diseases associated with expression of hematopoietic cell protein tyrosine kinase are provided.

13 Claims, No Drawings

SEQUENCE LISTING

<160> NUMBER OF SEQ ID NOS: 87

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide -continued

```
<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 2015
<212> TYPE: DNA
<213> ORGANISM: Homo sapiens
<220> FEATURE:
<221> NAME/KEY: CDS
<222> LOCATION: (169)...(1686)

<400> SEQUENCE: 3
cggaggcacg gaagatgagg aagatgatca ggaggatgat gaaggtgaag agggagatga   60
agacgatgac gacgatggct ctgaggggac ctcaggggct gccgagctgg ggggcgctc   120 aagctgcgag gatccgggct gcccgcgaga cgaggagcgg gcgccagg atg ggg tcg   177
                                                    Met Gly Ser
                                                      1 atg aag tcc aag ttc ctc cag gtc gga ggc aat aca ttc tca aaa act   225
Met Lys Ser Lys Phe Leu Gln Val Gly Gly Asn Thr Phe Ser Lys Thr
  5                  10                  15 gaa acc agc gcc agc cca cac tgt cct gtg tac gtg ccg gat ccc aca   273
Glu Thr Ser Ala Ser Pro His Cys Pro Val Tyr Val Pro Asp Pro Thr
 20                  25                  30                  35 tcc acc atc aag ccg ggg cct aat agc cac aac agc aac aca cca gga   321
Ser Thr Ile Lys Pro Gly Pro Asn Ser His Asn Ser Asn Thr Pro Gly
                 40                  45                  50 atc agg gag gca ggc tct gag gac atc atc gtg gtt gcc ctg tat gat   369
Ile Arg Glu Ala Gly Ser Glu Asp Ile Ile Val Val Ala Leu Tyr Asp
             55                  60                  65 tac gag gcc att cac cac gaa gac ctc agc ttc cag aag ggg gac cag   417
Tyr Glu Ala Ile His His Glu Asp Leu Ser Phe Gln Lys Gly Asp Gln
         70                  75                  80 atg gtg gtc cta gag gaa tcc ggg gag tgg tgg aag gct cga tcc ctg   465
Met Val Val Leu Glu Glu Ser Gly Glu Trp Trp Lys Ala Arg Ser Leu
 85                  90                  95 gcc acc cgg aag gag ggc tac atc cca agc aac tat gtc gcc cgc gtt   513
Ala Thr Arg Lys Glu Gly Tyr Ile Pro Ser Asn Tyr Val Ala Arg Val
100                 105                 110                 115 gac tct ctg gag aca gag gag tgg ttt ttc aag ggc atc agc cgg aag   561
Asp Ser Leu Glu Thr Glu Glu Trp Phe Phe Lys Gly Ile Ser Arg Lys
                120                 125                 130 gac gca gag cgc caa ctg ctg gct ccc ggc aac atg ctg ggc tcc ttc   609
Asp Ala Glu Arg Gln Leu Leu Ala Pro Gly Asn Met Leu Gly Ser Phe
            135                 140                 145 atg atc cgg gat agc gag acc act aaa gga agc tac tct ttg tcc gtg   657
Met Ile Arg Asp Ser Glu Thr Thr Lys Gly Ser Tyr Ser Leu Ser Val
        150                 155                 160 cga gac tac gac cct cgg cag gga gat acc gtg aaa cat tac aag atc   705
Arg Asp Tyr Asp Pro Arg Gln Gly Asp Thr Val Lys His Tyr Lys Ile
    165                 170                 175
```

-continued

| | |
|---|---|
| cgg acc ctg gac aac ggg ggc ttc tac ata tcc ccc cga agc acc ttc<br>Arg Thr Leu Asp Asn Gly Gly Phe Tyr Ile Ser Pro Arg Ser Thr Phe<br>180                         185                      190                      195 | 753 |
| agc act ctg cag gag ctg gtg gac cac tac aag aag ggg aac gac ggg<br>Ser Thr Leu Gln Glu Leu Val Asp His Tyr Lys Lys Gly Asn Asp Gly<br>200                      205                      210 | 801 |
| ctc tgc cag aaa ctg tcg gtg ccc tgc atg tct tcc aag ccc cag aag<br>Leu Cys Gln Lys Leu Ser Val Pro Cys Met Ser Ser Lys Pro Gln Lys<br>215                      220                      225 | 849 |
| cct tgg gag aaa gat gcc tgg gag atc cct cgg gaa tcc ctc aag ctg<br>Pro Trp Glu Lys Asp Ala Trp Glu Ile Pro Arg Glu Ser Leu Lys Leu<br>230                      235                      240 | 897 |
| gag aag aaa ctt gga gct ggg cag ttt ggg gaa gtc tgg atg gcc acc<br>Glu Lys Lys Leu Gly Ala Gly Gln Phe Gly Glu Val Trp Met Ala Thr<br>245                      250                      255 | 945 |
| tac aac aag cac acc aag gtg gca gtg aag acg atg aag cca ggg agc<br>Tyr Asn Lys His Thr Lys Val Ala Val Lys Thr Met Lys Pro Gly Ser<br>260                      265                      270                      275 | 993 |
| atg tcg gtg gag gcc ttc ctg gca gag gcc aac gtg atg aaa act ctg<br>Met Ser Val Glu Ala Phe Leu Ala Glu Ala Asn Val Met Lys Thr Leu<br>                      280                      285                      290 | 1041 |
| cag cat gac aag ctg gtc aaa ctt cat gcg gtg gtc acc aag gag ccc<br>Gln His Asp Lys Leu Val Lys Leu His Ala Val Val Thr Lys Glu Pro<br>295                      300                      305 | 1089 |
| atc tac atc atc acg gag ttc atg gcc aaa gga agc ttg ctg gac ttt<br>Ile Tyr Ile Ile Thr Glu Phe Met Ala Lys Gly Ser Leu Leu Asp Phe<br>310                      315                      320 | 1137 |
| ctg aaa agt gat gag ggc agc aag cag cca ttg cca aaa ctc att gac<br>Leu Lys Ser Asp Glu Gly Ser Lys Gln Pro Leu Pro Lys Leu Ile Asp<br>325                      330                      335 | 1185 |
| ttc tca gcc cag att gca gaa ggc atg gcc ttc atc gag cag agg aac<br>Phe Ser Ala Gln Ile Ala Glu Gly Met Ala Phe Ile Glu Gln Arg Asn<br>340                      345                      350                      355 | 1233 |
| tac atc cac cga gac ctc cga gct gcc aac atc ttg gtc tct gca tcc<br>Tyr Ile His Arg Asp Leu Arg Ala Ala Asn Ile Leu Val Ser Ala Ser<br>                      360                      365                      370 | 1281 |
| ctg gtg tgt aag att gct gac ttt ggc ctg gcc cgg gtc att gag gac<br>Leu Val Cys Lys Ile Ala Asp Phe Gly Leu Ala Arg Val Ile Glu Asp<br>375                      380                      385 | 1329 |
| aac gag tac acg gct cgg gaa ggg gcc aag ttc ccc atc aag tgg aca<br>Asn Glu Tyr Thr Ala Arg Glu Gly Ala Lys Phe Pro Ile Lys Trp Thr<br>390                      395                      400 | 1377 |
| gct cct gaa gcc atc aac ttt ggc tcc ttc acc atc aag tca gac gtc<br>Ala Pro Glu Ala Ile Asn Phe Gly Ser Phe Thr Ile Lys Ser Asp Val<br>405                      410                      415 | 1425 |
| tgg tcc ttt ggt atc ctg ctg atg gag atc gtc acc tac ggc cgg atc<br>Trp Ser Phe Gly Ile Leu Leu Met Glu Ile Val Thr Tyr Gly Arg Ile<br>420                      425                      430                      435 | 1473 |
| cct tac cca ggg atg tca aac cct gaa gtg atc cga gct ctg gag cgt<br>Pro Tyr Pro Gly Met Ser Asn Pro Glu Val Ile Arg Ala Leu Glu Arg<br>                      440                      445                      450 | 1521 |
| gga tac cgg atg cct cgc cca gag aac tgc cca gag gag ctc tac aac<br>Gly Tyr Arg Met Pro Arg Pro Glu Asn Cys Pro Glu Glu Leu Tyr Asn<br>455                      460                      465 | 1569 |
| atc atg atg cgc tgc tgg aaa aac cgt ccg gag gag cgg ccg acc ttc<br>Ile Met Met Arg Cys Trp Lys Asn Arg Pro Glu Glu Arg Pro Thr Phe<br>470                      475                      480 | 1617 |
| gaa tac atc cag agt gtg ctg gat gac ttc tac acg gcc aca gag agc<br>Glu Tyr Ile Gln Ser Val Leu Asp Asp Phe Tyr Thr Ala Thr Glu Ser | 1665 |

```
                485             490             495
cag tac caa cag cag cca tga tagggaggac cagggcaggg caggggtgc      1716
Gln Tyr Gln Gln Gln Pro
500             505 ccaggtggtg gctcgaaggt ggctccagca ccatccgcca gggcccacac ccccttccta  1776
ctcccagaca cccaccctcg cttcagccac agtttcctca tctgtccagt gggtaggttg  1836
gactggaaaa tctcttttg actcttgcaa tccacaatct gacattctca ggaagcccc   1896 aagttgatat ttctatttcc tggaatggtt ggattttagt tacagctgtg atttggaagg  1956
gaaactttca aaatagtgaa atgaatattt aaataaaaga tataaatgca agtcttacg   2015

<210> SEQ ID NO 4
<211> LENGTH: 20
<212> TYPE: DNA
<213> ORGANISM: Artificial Sequence
<220> FEATURE:
<223> OTHER INFORMATION: PCR Primer

<400> SEQUENCE: 4
tttgtccgtg cgagactacg                                              20

<210> SEQ ID NO 5
<211> LENGTH: 19
<212> TYPE: DNA
<213> ORGANISM: Artificial Sequence
<220> FEATURE:
<223> OTHER INFORMATION: PCR Primer

<400> SEQUENCE: 5
ttgtccaggg tccggatct                                               19

<210> SEQ ID NO 6
<211> LENGTH: 29
<212> TYPE: DNA
<213> ORGANISM: Artificial Sequence
<220> FEATURE:
<223> OTHER INFORMATION: PCR Probe

<400> SEQUENCE: 6
ctcggcaggg agataccgtg aaacattac                                    29

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                               19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                              20

<210> SEQ ID NO 9
<211> LENGTH: 20
```

```
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                          20

<210> SEQ ID NO 10
<211> LENGTH: 30000
<212> TYPE: DNA
<213> ORGANISM: Homo sapiens
<220> FEATURE:
<221> NAME/KEY: exon
<222> LOCATION: (4334)...(4437)
<223> OTHER INFORMATION: exon 5
<221> NAME/KEY: exon:intron junction
<222> LOCATION: (4437)...(4438)
<223> OTHER INFORMATION: exon 5:intron 5
<221> NAME/KEY: intron
<222> LOCATION: (4438)...(8453)
<223> OTHER INFORMATION: intron 5
<221> NAME/KEY: intron:exon junction
<222> LOCATION: (8453)...(8454)
<223> OTHER INFORMATION: intron 5:exon 6
<221> NAME/KEY: exon
<222> LOCATION: (8454)...(8603)
<223> OTHER INFORMATION: exon 6
<221> NAME/KEY: exon:intron junction
<222> LOCATION: (8603)...(8604)
<223> OTHER INFORMATION: exon 6:intron 6
<221> NAME/KEY: intron:exon junction
<222> LOCATION: (8950)...(8951)
<223> OTHER INFORMATION: intron 6:exon 7
<221> NAME/KEY: exon
<222> LOCATION: (8951)...(9103)
<223> OTHER INFORMATION: exon 7
<221> NAME/KEY: exon:intron junction
<222> LOCATION: (9103)...(9104)
<223> OTHER INFORMATION: exon 7:intron 7
<221> NAME/KEY: intron
<222> LOCATION: (9104)...(11187)
<223> OTHER INFORMATION: intron 7
<221> NAME/KEY: intron:exon junction
<222> LOCATION: (11187)...(11188)
<223> OTHER INFORMATION: intron 7:exon 8
<221> NAME/KEY: exon
<222> LOCATION: (11188)...(11367)
<223> OTHER INFORMATION: exon 8
<221> NAME/KEY: exon:intron junction
<222> LOCATION: (11367)...(11368)
<223> OTHER INFORMATION: exon 8:intron 8
<221> NAME/KEY: intron
<222> LOCATION: (11368)...(13127)
<223> OTHER INFORMATION: intron 8
<221> NAME/KEY: intron:exon junction
<222> LOCATION: (13127)...(13128)
<223> OTHER INFORMATION: intron 8:exon 9
<221> NAME/KEY: exon
<222> LOCATION: (13128)...(13204)
<223> OTHER INFORMATION: exon 9
<221> NAME/KEY: exon:intron junction
<222> LOCATION: (13204)...(13205)
<223> OTHER INFORMATION: exon 9:intron 9
<221> NAME/KEY: intron
<222> LOCATION: (13205)...(18422)
<223> OTHER INFORMATION: intron 9
<221> NAME/KEY: intron:exon junction
<222> LOCATION: (18422)...(18423)
<223> OTHER INFORMATION: intron 9:exon 10
<221> NAME/KEY: exon
<222> LOCATION: (18423)...(18576)
<223> OTHER INFORMATION: exon 10
<221> NAME/KEY: exon:intron junction
<222> LOCATION: (18576)...(18577)
<223> OTHER INFORMATION: exon 10:intron 10
<221> NAME/KEY: intron
```

<222> LOCATION: (18577)...(23563)
<223> OTHER INFORMATION: intron 10
<221> NAME/KEY: intron:exon junction
<222> LOCATION: (23563)...(23564)
<223> OTHER INFORMATION: intron 10:exon 11
<221> NAME/KEY: exon
<222> LOCATION: (23564)...(23695)
<223> OTHER INFORMATION: exon 11
<221> NAME/KEY: exon:intron junction
<222> LOCATION: (23695)...(23696)
<223> OTHER INFORMATION: exon 11:intron 11
<221> NAME/KEY: intron
<222> LOCATION: (23696)...(25876)
<223> OTHER INFORMATION: intron 11
<221> NAME/KEY: intron:exon junction
<222> LOCATION: (25876)...(25877)
<223> OTHER INFORMATION: intron 11:exon 12
<221> NAME/KEY: exon
<222> LOCATION: (25877)...(26412)
<223> OTHER INFORMATION: exon 12

<400> SEQUENCE: 10

| | | | | | |
|---|---|---|---|---|---|
| gatcttctcg | cctcagcctc | ccaaaatgct | gggattatag | gcctgaacca | ctgcacctgg | 60 |
| cccatccctc | atttgattca | ttcgacaagc | acatgctcat | gactcttcaa | gccctgtgcc | 120 |
| agcctaaggg | gctgtggaaa | caaataagat | atatccctac | cctcaaggag | ctctccataa | 180 |
| cccatcgttc | ttggctgtgg | gttcttcttg | tgtctagctt | gactctaaaa | atatacttca | 240 |
| gtcatccatc | catccatcca | tccattcatc | catccatcca | tccatccatc | catccatcca | 300 |
| tcatccaaca | gatacctgtt | gattccctat | tccagggtta | aagatgact | tagatggggc | 360 |
| tccctgctgg | agatgttctc | tgtatggtgg | atgaggttga | tgagtaaaaa | gatgactaca | 420 |
| ttgtggggtg | gcaatacatc | ccattaaaaa | ccagccaatc | aaaagttgac | aaatgacagt | 480 |
| ccccattgtt | ttgtctcttc | tgcctcctct | ttctagctag | atggtattat | gggtttggga | 540 |
| tgcttgcctg | ttaaaaatga | aaacgcttag | gcttttccca | ttataaagcc | acctccttct | 600 |
| ggctgggcat | ggtggctcac | acctgtaatc | ccagcacttc | gggaggccaa | ggcacgcaga | 660 |
| tcacctgagg | tcaggagttc | gagaccagcc | tgaccaacaa | ggtgtaaccc | catctctact | 720 |
| aaaaatacaa | aaaaaattag | ctgggtgtgg | tggtgcgtgc | ctgtagtccc | agctactcgg | 780 |
| gaggctgagg | caggagaatc | acttgactcc | aggggggcaga | ggttgcagtg | agctgaaata | 840 |
| tcatgccact | gcactccagc | ctgggggaca | agagcgatac | tctgtcaaaa | aaaaacaatt | 900 |
| atgtcacccc | ttcttagtga | tcatggaact | gggggctctt | agctgtttct | ctctccttct | 960 |
| tccaggcttt | gccctgggtc | atcccatgct | ctgtttctcc | actccagggt | ctgaacactt | 1020 |
| acagaatccc | tgggtcacct | catgtagtcc | ttgcagcaac | catggaggag | gcgtggctgg | 1080 |
| cattatttct | caaaggcaac | ataattgcta | agtggaaaac | gcagggtgta | gacaacatga | 1140 |
| atgggggtt | atcatttgca | gacaaaggca | aaataaccta | gatgggggt | tctcagacat | 1200 |
| gagcagcaac | agcatcacct | ggattgccgg | ctaacaagtg | ctttctgggc | tccactgtca | 1260 |
| gattccgaat | gtgcatttct | aacaggttct | tgggtgaggc | agctgctgct | gctgctgctc | 1320 |
| cagggaccca | gcttgggaac | cactgatcta | aatacgcata | tctggccagg | tgtggtggct | 1380 |
| cacacctgta | atcccagcac | tttgggaagc | cgagggaggt | ggaacacttg | aggtcaggag | 1440 |
| ttcaagacca | gcctggccta | catggtgata | ccctgcctct | actaaaaata | caaaaattag | 1500 |
| ccaggtgtga | tggcgggctc | ctgtaatccc | agctactcag | aggctgaggc | acgagatttg | 1560 |
| cttgatctgg | gaggcagagg | ttgcagtgag | ccgagatcac | gccactgcac | tccagcctgg | 1620 |
| acaacagagc | gagactctat | ctcaaaaaat | aataataaaa | ataacaaatg | aatacacata | 1680 |

-continued

```
tgtgtcctttt caggggactc aggggtcctt gtgtctgaat caagaaactg ctaacagagg    1740
ttgcctctgg ggagcacaac tgggaccttg ggaatcaggg cgggatggaa tcttggtttc    1800
tctcattctc ccttgaaata ggcaatactt tcaaatgttt caaaatgcaa atgtggggaa    1860
gcatgcagaa gagtgaaaag tcttcttccc accctgtccc caaccagcca cttccctcc    1920
ccagaagcaa ccagtttctc gtgagtcctc ccagatgctt cctccttata taagaaaaga    1980
catctcttcc cgcttatctc acacaagtgg tagataccac acacactgtt ccatgcctct    2040
cgttcagacc ttccatgcag caccttgttc ctgttttgtt ttgttttgtt ttgttttgtt    2100
ttttaggtgg agtttctctc ttgttgccca ggctggagtg caatggtgtg atctcggctc    2160
actgcaacct ccgcctcccg ggttcaagcg attctcctgc ctcagcctcc caagtagctg    2220
ggattacagg catgcgccac catacctagc taattttgta ttttaatag agacagggtt    2280
tctccatgtt ggtcaggctg gtctcgaact cctgaactcg tgatcctcct gccttggcct    2340
cccaaagtgc tgggattaca ggcgtgagcc actgctcccg gacacctcct tccttttat    2400
accacagggc gtctgtcctg tagatgtcct accgtccatt taacctctgc cctatacagt    2460
ggtcacttaa gttgttttcca gtcatgtact gaagcgaatc tcctggtgta tatgtcattt    2520
ctcccttgtg caaggtctat gggataactt cctaggacca gaattgtcag ggagacagtt    2580
ggtttttttt gtttgtttgt ttgtttgttt ttgagacaga gtctcgctct gttgcccagg    2640
ctggagtgca gtggcgtgat ctcggctcac tgcaagctcc acctcccagg ttcacaccat    2700
tctcctgcct cagcctcccg agtagctggg actacaggct cctgccacca tgctcggcta    2760
atttttttttt ttttttttgt attttttagtc gagacggggt ttcaccatgt tagccaggat    2820
ggtctcgaac tcctgacctc gtgatccacc cgcctcggcc tcccaaagtg ctgggattac    2880
aggtgtgagc caccgcgccc agccggggga gacagttctt agtcttacat agttgaatat    2940
tttaccatgg cacaagtcac tttacaacat gaaagcaaag aaggtagatg agcaacatag    3000
catggtgatt cagagcttgg gttctggagt tagactgcct agcttcaaat cctgcctcta    3060
caacttccca gctgtgtgac tctaggcaag tcacttgccc tctctgttcc tcaatttcat    3120
catccataaa atggggccag gagcagtggc tcatacctgt aatcccatca ctttgggagg    3180
ccaaggtgga tggatcacct gagttcagga gttcgagacc agcctggcca acatggtaaa    3240
accccgtctc tactaaaaat acaaaaatta gctaggtgta gtggtgggtg cctgtaatcc    3300
cagctgcttg ggaggctgag gcaaaataat tgcttgaacc cgagaagcag aggtttcagt    3360
gagcccagat cacaccactg cactccagcc tgggtgacag agcaagactc agtctcaaaa    3420
aaaaaaaaa aaaaaaaaag gggggaatg ataaaggtga caactccata gagctgttgg    3480
gtggatagca agatagatgt taacttcctc cccagttgat aacagaggaa ccaaaggccc    3540
aaagaggaag gcaacttgct caaagtcaca ctgcaggttt gtggcagagc caaggcaggc    3600
tgaggtcagg tctggggctt ttttccaact gctcctcacc ccagtgaagg tgggaatgga    3660
ttccactgct gctgcttgaa cttttccacc caaatatctc aatattcagg aagaatgaag    3720
aaaatgtccc aggatataat cctaagtata aaattctttc caatctcaca ttgtagctta    3780
gaagttcagg ccaactttat attcaactcc atatatgcgg aggaggattg gttgtaaagc    3840
taacaaaact caggccttc acaggcttcc aaggtcccaa gaaggatctt ccccgtggtc    3900
ttgtatgctt gtgaaacctg caaaagtaag actttgacca cagctggtta agactgctgt    3960
ctgtttccac tctgtcttcc tgtccatctc cctgtccctc acagcgagca gcactgaaat    4020
gacctatcag cttttttgcac ttgttaatgc tgtattattt ttcttaaagg aagttccccc    4080
```

```
actccaaatt gcataggctt cagtctcagc aaacaggatt cacttcgggt aaaatgtcta  4140
ttttgatatc aaaagaatgg ctcctttacc ttctctcccc caaaaaatct ttgagtaaaa  4200
ctgatgctgc aggaagccag accctctgta tcctgacatt cccctgggac ctgcatggcc  4260
acaggcatcc tgtgtaggcc ggacaggact gcatgacccc aggttcacat ttgtcccctc  4320 cctttccat caggtggttt ttcaagggca tcagccggaa ggacgcagag cgccaactgc  4380
tggctcccgg caacatgctg ggctccttca tgatccggga tagcgagacc actaaaggtg  4440
acaccagccc tccccacctt gtcctccctg ccgaggtgcc ccagctgggg ctggccacca  4500 cccttttcctt ggaaaatgcc ctgggaaagg ctgaaaaacc caaccaggtg ctgtggctgc  4560
caggtttctc ctgctcttgg ccacctgagc tggggagggt tgaggctctg tgcctggctc  4620
tgcccttctt atccaccata gctgccagct taggtcagtg aactagtgc caggtggctt  4680 aggccctgaa aacaaagaaa catccagctg aagcttgatc ttcactgact tgtttttttca  4740 tttgttttgg ttcttgtttt gttttgttct gtttttttgag atggagtctc actctgtcgc  4800
caggctggag tgcagtggtg cgatctcggc tcactgcaac ctccacctcc caggtttgag  4860
cgattctcct gcctcagcct tccaagtagc tgggattaca agtgctcgcc accatgccca  4920
gctaattttt gtattttttag tagagacagg gtttcaccat gttggccagt atggtctcga  4980
tctcctgacc ttgcgatcca cccctcttgc cctcccaaag tgctgagatt acaggcgtga  5040
gccactgcgc ctggcctgtt ttgttttgtt tgagacaggg tctcactctg ttgcccaggc  5100
tggtatgcag tggcacaatc tcagctcact gcaacttctg cctcctgggc tcaaatgatt  5160
ctcccatctc agtctcccga gtagctggga ctacaggtac gtgccaccat gctgactaat  5220 ctttctttc tgttttctt tctttcttt tagtagagat ggggttttgc catgttgcct  5280
aggctggcct cgaacttctg gactcaagca atctgcctac ctcagccttc caaagtgtca  5340
ggactacaaa gtgtcaggat tgttttttgtt ttggtttttt taaatacccg taacagacca  5400
agtaggggag gccaacacag gaggatcact taagcccaaa agttcgagac cagcctgggc  5460
aacatagtga gacccatct gtatgaaaaa ttttaaaaat tagccaagca tggtggtgca  5520
catctgtact ccctgatact cagaagggtg aggccagatg atctcttgag tccaggagtt  5580
caaggctgca gcgagccata atggagccac tagactccag cctgggcaac agagcaagac  5640
cccatctcta aaaaataaa acaaaatacc cattacaata gatcttatcc acaagcctca  5700
ttcctccttt cctccctcca taaggaaatg aggtaggat aggtcgccag aagagactca  5760
agccagcctt ctctgggact ctgctgaaaa tgctccttgg aagcttttgg aagttttaat  5820
gtcaggtgac cagcttcctg gaatttctgt gctgcaaggg tggattcatg ctgattgggt  5880
gcatggatgg caagaacagg cctggaaaac atcgcgtagc tcaaactggc atcgattgag  5940
gctcattgcc tcaaaggaat gaacatcagt aggattctta tgatttcaga tttcatgtgc  6000
taagtgcacc tttactaata catttaggtt cacaactgct tgactcaaat aagccaagta  6060
tattgtataa tatgtgacct cacggtaccc tgaagcaaac agatttgggg acattgatta  6120
aaggcatgtt cctcatgtgg ccttctactt gaccctcagc tatctgaatt ggcgaagctt  6180
tcatgtggct aggataatgc tacccacaat cagtgtggca gctcagtgaa tgcctgggct  6240
ttgtctcttc ccacccaacg agcccattc aagcccccag ggggaagaaa aggagataaa  6300
aagacaaagc tgtgcacagc ccagcgcttc tcctctctag ctgtgcccag acagcttttt  6360
ggcttgggct ggtccatcct gcagacaagg gcagagaaat caaagaaacc atcacagatc  6420
```

```
tgtggggcag gaaaatgagc ctggtccagc tttcacagct ctctgagatg gggcatgttg    6480
ggaattttag ccgatttaat aaaagttgca gcatgagacc tgtgaatccc accctgctgc    6540
ttcctggatc ctgccacacc ccatccagca gcaaccaagc cagtctcgcc cctgactggg    6600
acagagtggc tgagagggc tctggagcca gctgcctgga tttgaatccc agctgtgcca    6660
cttaccagct gtgtgactgt aggtgagtta tttcacctct ctgggcttca gtttcctcat    6720
ccgtaaatga ggatgatgat attataaaac ccttaccccca tgaggttatt cattcattaa    6780
ataaataata ttataattta tatagttata attcattata atgaatatta ttcttattca    6840
ttcattgttc atctacgcag agtgcttttga acttgcctgg catgtacggt aagctattat    6900
tcattcaaca gtataaactg gccaggtgag gtgactcaag cctgtaatcc cagcagtttg    6960
ggaggctgag gcatgtggat cacctgagct caggagttgg agaccagcct ggccagcatg    7020
gtgaaactcc atctctacta aaaatacaaa aattagccgg gcgtagtggc gggcgtctgt    7080
aatcccagct actcaggagg ctgaggtagg agaattgctt gaacctggga ggcagagatt    7140
gcagtgagcc aagattgcgc cactgcactc cagcctggat gacacagcga gactctgaca    7200
cacacacaca aaaaataaag tttaaacttc ccaaatccta tgacattgta ctattatcat    7260
ggtaaagaac actgagacag agggactaat aacttgccca agggcacaca gctcacaaat    7320
agcaaaacgg tggtcatgag ctgaaagact tatgtgtttc tgctctatgt gataatatag    7380
ggtggtgcaa aagtaatttc agttttttcc actactttg aaggcaaaaa ctgcaattac    7440
ttttgcacca gcctaatatg tatgttaggt tcccattgct gctgtaacaa attaatacaa    7500
acttagtggc ttaaaacaac acccgtctat tctctaacag ttctggggat cagtagtctg    7560
acctcactgg gctcaagatg tcagcagggc tggttccttc tggaggcttc aggggagaat    7620
tcattttctt gcctttttta gtttccagag ctacagcat tccttggctc atagtccctt    7680
cctgacatct gtccaagctc ttgttttccat cttcacctct tccactttga ccttcctacc    7740
tccttctaac aagaactcaa gggattacac tggggctacc tggatcatct ggaataatct    7800
ccccgtctcc agatccttaa cttaatcaca tctctaaagt acctttttacc atgtaaggta    7860
acatattccc aggttccagg gtttagggca tgactatctt gagggaccac tattcagcct    7920
accacagcat gttcacattt caataactgg actggatttc tgggttttttt tccagaaaag    7980
tcatagcctg agtttttatg aaaaagtaaa aagtatacta tggtctcttg gcttttttgta    8040
gggtagatga tagaaagatg gaacaataga tcagaaataa tgaagatgat gatgatgata    8100
gccaacattt gcagagtgtt cagcttccaa gtagtttaca ggcattactt cttttagccg    8160
tcaggcaata ggatcaggta gggaggcgtg agaactattc ccattttaca gatgagaaaa    8220
ctgaggcata gagaggtgac atagtcacat ggccaaggtc tcacgggtgg atgtggtaga    8280
gcctggatga gagcccagga tgcctggctc ccacagccca ctcagaccct cgggcacttc    8340
tgcccaggtg tcaggacggt gccagcggta gccttacagg gtgtcagagt gctaatgcaa    8400
ggtggcaggc ctccaagatg ccattctgag gggtttctct ttggtcaatt caggaagcta    8460
ctctttgtcc gtgcgagact acgaccctcg gcagggagat accgtgaaac attacaagat    8520
ccggaccctg gacaacgggg gcttctacat atccccccga agcaccttca gcactctgca    8580
ggagctggtg gaccactaca agagtgagtc ccaccccagg ggtgacatcc ccaccacgat    8640
gggcccacag actcctagtc acggatgcac tgtggcccct gagacctgct gtgtccttct    8700
tggccatccc ctagacagat agttgctttg gatgcttctg aaggcttagg actgttgagc    8760
aggagggtga ggtggccaag atgtagaggt ggcacccccgt cacactctgc ttgcttggga    8820
```

-continued

```
atgtctctga tggtggcaac caggtggaac actggagaga tccagtggac caggtagggc   8880
ggcctccaag gagcaacctc tggctggctc ggtgcttgtt gctctcaatt gaccagggac   8940
tctgttccag aggggaacga cgggctctgc cagaaactgt cggtgccctg catgtcttcc   9000
aagcccagaa agccttggga gaaagatgcc tgggagatcc ctcgggaatc cctcaagctg   9060
gagaagaaac ttggagctgg gcagtttggg gaagtctgga tgggtaagga cccagggcca   9120
cagcccacag ggccagaggg tggaggggag agggaggcca cttgcttcca ggaacacctt   9180
atggcaaagc gggaatgcta cccaaggcag agggggagat ttaaataata gccataaaga   9240
agcagttccc tgatagcaaa ccaaattgtc ttgctgtgca aacactgatt tgcctttgag   9300
accagtcctg tagtggtcaa aaacttcctt ctgggaagca ggtgtcatgg atgaggaatc   9360
cctccctcat acggagtggg gactgcctaa cagtttggga ttgagataac cagagacctt   9420
ttcagatgat gaaaattaag aatggggaaa tgcagcttgg agatttccag gcaactgatg   9480
aacaggttat tctgagcacc tgctgtgtgc ccagcactgt tagggtcttg tgggaaaatc   9540
agaaaggcac atctcacacc tgctgatttt ccccaagaac ttaagaacaa cactgcctgc   9600
tttgcagggc tgtggggtag atgcagtgcc agcccagtgt ggggcagcct gctgtgttaa   9660
tacgttccaa atgggagcgt tccaaatggg agcgaagaca acttacaggg atgcaaacaa   9720
ctcagccaga taaaataagt ttaaaatcca tgtatttcga ctgtatttat tgcgattctg   9780
ctgcatgcaa ggccgggcac agtggctcac gcctgtaatc ccagcacttt gggaggccga   9840
ggcaagtgga tcaatcaagg tcagcagttc gagaaaaacc tggatagtat agtgaaatcc   9900
cgtctctacg aaaaaataca acaattagcc aggcgtggtg gtgggagcct gtaatcccac   9960
ctactcggga ggctaaggca ggagaatcgt ttgaacccag gaggtggaag ttgcagggaa  10020
ccgagatcgc accactgcac tccagcctgg gagacagagt gagactctgt ctaaaaaata  10080
ataataaaat taaaagaat ttgacaaaaa agaaaatatg gagaggaagg taagacagat  10140
ctgagtggtg agatttgaaa gccaaaaata tcatataaga cgctagactc ctactacagg  10200
aagcccacgg ttctggattg gagcttcctg gaagccaagg caaaatggaa acccaagcaa  10260
ttataaaatt gacaagaccc accaaatgaa gcagggtggg gtgaggggag ggaacagcat  10320
gtgccaaatc cctgtggtgg gaggtgagtt gggtgcttga gggactgagt gacctgcagg  10380
gtgactggca cataaaaggc aaggggagtt tagtggctga tgaggctaga ggggtggacg  10440
aggctgggtc atgtagggcc tgggggtcat agtaagtctg gcatttattt aagagcagtg  10500
ttaagattaa agtgggcggt gtatgtgtgt gacataacct gagtagtgtt ttaaagctat  10560
ttttatttgt ttgggttttt tgtttgtttg tttgtttgag acagagtctc gctctgtcac  10620
ccaggctgga gtgcagtggc tcaatcttgg ctcactgcaa gctccgtctc ctgggttcac  10680
accattctcc tgcctcagcc tccccagtag ctgggactac aggcgcccac aactgcgcct  10740
ggctaatttt ttgtattttt agtagagacg gggtttcacc gtgttagcca ggatggtctc  10800
gatctcctga ccttgtgatc cgcccacctc ggccccccaa agtgctgaga ttacaggcgt  10860
gagccactta gagctatttt taaatccttg caacagcact tcaaaggcaa agcttaccat  10920
ttccacttta cagatgagga agctgaggaa gccacggctc agagacgtta agccacttgc  10980
cctagtgtgc acagctggga agtggtgaac ccgcctttca acccacagtt gtctgaggcc  11040
taagcccatg atttcgcttc cctctctgag agttgagatg agcaggaaag actttctgga  11100
ggaggcgggt ctgcagctgg gccttctagg gtggtacggg agaccagtgg gctctgacca  11160
```

```
ccttccctgc tctctatccc cctccagcca cctacaacaa gcacaccaag gtggcagtga    11220
agacgatgaa gccagggagc atgtcggtgg aggccttcct ggcagaggcc aacgtgatga    11280
aaactctgca gcatgacaag ctggtcaaac ttcatgcggt ggtcaccaag gagcccatct    11340
acatcatcac ggagttcatg gccaaaggtg ctgcgtgctg gggctggggg tgcaggctgt    11400
ggcctatact ggtcaattgc gggcccaagg gtggcttgga catggttctt gcccttgaga    11460
tggccccaat ctggccagga gctcttccaa caagtactca ttgagaatct aatgtggaac    11520
aatccagccc tcctggttag tggggtgaaa tcatgttaag gggtcaccaa ggggaaggga    11580
gaacaagggg ctaccaggag aagggaatgg ggccagaata ctcctgggca atgggagaag    11640
gggcttatgg ttcacagtga gccttagagg ccagggtgtg gcatggtggg tgggggtgcc    11700
actctcccgc atcagccacc ttccctgtac ttgccaaagc cctgggagag ggagctggca    11760
aagcagcagt tctgccccca ccccgccct gccacaactc aggatttctt ggggaatttt    11820
tttaggccac tgtttcacaa ccattttcaa cccctgccat tttttgtttg tttgttttt     11880 agggacagga acttgctctg ttactcaggc tggagtgcag aggtgcaatc ataactcctg    11940
ggctcaagtg atcctcccac cccagccccc cgagtggctg ggaccacagg cccatgccac    12000
cacactcagc taatttat tatttattta catatttatt tttagagaca gggttgccct     12060
ctgcctaccc aggctggagt gcagtggcgt gatcatagtt cactgtagcc tcaaactctc     12120
aggctccagg atcctcccga cttagtctcc ccagtagctg gcactacagg catgcactac    12180
cacacccagc taatttctaa aaaatttt ttttttttg agacagagtc tcactctgtt       12240
tcccaggctg gagtgcagtg gcacaatctc ggctcaatgc aagctccacc taccaggttc    12300
acgccattct cctgcctcag cctcccaagt agctgggact acaggtgcct gccaccatgc    12360
ctggccaatt ttttgtatt tttagtagag acggtgtttc accgtgttag ccaggatggt     12420
ctcaatctcc tgaccttgtg atccgcccgc ctcagcctcc caccatgctg gaattacagg    12480
cgtgagcaac tgcgcccagc ttctaaaatt tttttctaga acaaggtct cgccatcttg     12540 ccccagctgg tctcaaactc ctgggttcaa ctgatcctcc caaagctttg ggattatagg    12600
catgaaccac tgagcctggc ctaacatata tatttgtaaa ttttctatctat agatggggtc  12660 ttgcgatgtt gcccaggctg gtctcaaact cttggcctca ggtgatcctc tcacctcggt    12720
ctcctaaagt gttggaatta caggagtgag cctcgtgcct agccactctg cccatttttt    12780
gataaacaga atcatctcat gcaatcccat ttagtgcgat ttgaaacctc aagccttttt    12840
cattttaact atgcaattat gccagtcctg tgaaggcatg atcccagcca tccaggctca    12900
ggggctgtct cagtcacaga atccatctag caatcaaaaa gtcacttcac taaaactcaa    12960
ttctctttct caaacactag gaattgcaaa caaatattcg tatttaaatc tactactatg    13020
aaaaatcttc accacacact aaagtactag attggtgcaa aagtaattgt ggttttgcc    13080 attaaatagt aaaagtagta aatgttcctc ccctctcccc catataggaa gcttgctgga    13140
ctttctgaaa agtgatgagg gcagcaagca gccattgcca aaactcattg acttctcagc    13200
ccaggtgaga gcctaacgag gaaacgggga agggaaacag gaattcgatt tttttacttg    13260
ccaaatattt actgaccaca tactatgatg atagcagtaa taataatggg taaaatgtat    13320
tgagagctca gtataaaact atgttttttg catatatttt attatacatg tactcattca    13380
tttaatcatc ctataagctt tataggctgg gatttttgtt atctatttg gtataacaaa     13440 ccatccaagt cctagtagct tgaaacaaca gcaattgtta tttctcatga tcctgtgggt    13500
tgcctgggtt cagctgggtg gttcttctgc tcgtcatggt aaagtgaggt gcagatgttg    13560
```

```
gcacttgccc aggctagaat gtccaagaca tggctcagcc tccagggtct ctccacatag   13620
cccctcacca cccaatcacc cagcctgagc ttcttcacgg cgcagcagct gggttccaag   13680
acagagctgg accaggggcc aagccttcat gagcaggctc tcattaagcc tctgcctgca   13740
tcaggcttgc taatggccca ttggccaagt cacatagcca tgcccagaat cagtgtggga   13800
ggggactgac caaggacaca aatcccaggg accccctcaa tgtaacagtc tggccacaga   13860
gtaggtaatt atcatcccat tttacagaat aggaaattga agcatagagc agaagtaaag   13920
tacagatgtg gaaactgagc cccagtgtgg ttaagtggct tgcacaagtt actgtgctaa   13980
ttatggggga tatagcagtg aacaaaatga aaatgttcct gtcctaatag agttcacaat   14040
ccaggtggga agatgagtat taaataacca aatctcttag agaccatgac ccaagtggtc   14100
ctggctgagt caaaagagca cagtatctaa caaagtaaat aatgttcaca aatcgcaaaa   14160
acactgctga aaacctaatt ttctttctca tgttccccac gccccttgca gctcctctca   14220
cccccagcct aagcagtttt ttcacttctg tcctctctca tgctctctct gatgtctggg   14280
aaaacagagt gtaaggacgg ggtggtatta gagtgcatag ctagagcatt tagcctggtc   14340
caggagcaat cagagaatgc ttcctggagg aagtggcctc taggccgagc ctgaaggatg   14400
aatagaagtt cagtagatga agagaaaagg taaaggtctt ttagacaaaa gaaacagcct   14460
gtgcaaaagt aggtgaagga gttcagccta ctcagcagga gcccagggat agtgggagtt   14520
gagtgagacc ctgcctgggc ctcagctggg cctgctggag atgccaaggg cagggctcat   14580
ttgagtatgc aaattcaggg gcccagagga caccacaaag tgtaacaaaa gactctactt   14640
tcagagcctg gaatgccaga ggcatatgga aatgtgtttt cactcctatg ggccaggtcc   14700
tctgggagac aatagactgg tctgttgcta aattatcatc ttcaaactag cagaagccct   14760
gctgggcagc agtcaccgac cagggcaaga gccactctgc ccgtttcaca gagggggaaaa   14820 caaaccaagg gaggaaaaga ggttctgggc cttcatctgt ccagaagcag aggtagattc   14880
agagcccagg gacagaaagg agcccacctg gggctttggt cttcacctcc agactcagag   14940
aggcagcttg gagcagcagg tggagaactg gaccacacat gtggggtttc tgtagtcaca   15000
gctttgtggg tgacatgaaa tgttattcag tagctgcata tatacaaaca ggtcaaaaca   15060
gagctgctct gactgaagca gggtgggggg cttatctgtg gcctttcttt tgtctccccc   15120 accccccatat aaccttgagg catccatagg attcagttgg aagagctcta caggtccttc   15180
cagctctgat gctgtgactc cctgatactc tttggaagca aacccaaggg tgcccaacct   15240
catggcaccc tatctggggg tcatgaaatc tcaccgcctt tatcaacccg cagtgcttac   15300
acctgggccc aataaaccta ctcgttattc attcagtcag cagaccctgg agaagcaaca   15360
ctattagcat ctgggcttag gagtcacaca gagttttgtt ttgatctcag ctctgcctgt   15420
gtagcctcaa gcaagttgct taacctctct gagtgccact ttcccccact gggagcactg   15480
ggagccactc tttaaataaa tacttaacta tgtgccaaac actctactaa gcccttgatg   15540
taggcttagg ggattcatct tcacatgacc ccttggaacc aggtgctatt acagagaaga   15600
aaagtgaggt acagagagat gacacaactt gcttgacatc acagagctgc agcgctcaag   15660
ctgagttggt ccagctccag agccatttag ctattaccct ctgctgtctc ctaagtgggg   15720
tgtcatccct gccccatcga gctcctgtga aaatcagtag catatgagca tctgccagtg   15780
agcatcaaac agtggtaact accagcatta gtccttgctc cagaagaaaa gcaaggcaaa   15840
aaagctgggc caagtaacag gtaagtgcgt ggaccccaag cagcgctttt ggagctccag   15900
```

```
ccctggctcc gcaacttgca agctgtgtaa gctggggcca cttacctatt tctctgggct    15960
tcagttttct tatctgtgga aatggggctg ataacaaaag tgcctcctcc aaagcacatg    16020
gtaaatgtca cataagtgtt taagtatcat cttataaata agctatgatg ccttccatta    16080
gcatcataac ttttgttaac tgttcatcta aggactcata aatttcccac actcccaggg    16140
ccaagatgct gtctcactcc accctggcaa cctcatcccc atttcgtccc caccccccac    16200
tattctaaac aaaatcagag tctcttccaa gttttttactg aaaaatttgg gtctctgggt    16260
ctcccttggg catgacagct caggcctgta atcccagcac tttgggaagc tgaagcagga    16320
ggatccttta agcccagcct gggccacata gtgggaccct ttctctatta aaaaaaaaaa    16380
aaattctttt taaatttaat ctggcatagt ggcatgcacc tatagtacca gctgcttggg    16440
aagctgaggt gggaagactg cttgagccca ggaggcacag gttgcagtaa gctgtgatcc    16500
caccactgta ctccgtgaca gagcaaggcc ctgtctcaaa agaaaaaaaa aaagaagaaa    16560
gaaaagaaaa aagcaaagca tgggtctcca ttctaactgc ctcgggtgcc ccctgctgtc    16620
caccccttgc aagtgcgcca cccacttgcc tcagaccttg agaagccggc cggtggtgct    16680
ttgattgttc tgtctagtca gacgccctca cttccagaat aatttcatca gactgcaccc    16740
agctgcagtc tgccggagca ctggagtgct gggttattta gaggcagcag gatgcactgg    16800
attgggagtc ctcagactgg tttgagcctg acattcagaa ttttcctggt ggtgtgatct    16860
ggaacaagtg gttccatgtc tgtaaaacag agattatgat cattcctgcc tcaaagagct    16920
caagcccagt ttgtaaacca aaagtgctgc tttctgggca tctgagggtt catcttcaac    16980
cgcttttgtc caaacccttg taagtaaaaa tgtctgcaag atataatccc tgtgttttca    17040
tcagaggctt ctagggctcc tggtgtgaat aagaatcctc cacgcagtct gttagtcact    17100
cagcagccat ggtgatcttt aaatgtacat cagaacatgt cacgctcctg ctcgaaggcc    17160
tctaatatct ccccaacacg ctcagaataa aatccaccct cctctcctga cctacaaggc    17220
agttcatgat tggcggcctc cctctcaact tcaactctcc ccactctctc tgtggcatct    17280
tctgctggcc acactgacct ctgtgctgtt ccatgaacac ccaagctctt acctacctcc    17340
acgcctttgc atctcatgtt ctctctgcct agaatattct tatgcgacac acttattatt    17400
atcatcattc agatctttgc taaaatctca ccccctcaaa gcaggtttcc ctgaacgccc    17460
aatccaaaaa agctctctac aggtcatatt ttgttacttt gttttatctt ttttttcttt    17520
ttgagacaga gtcttgctct gtcgcccagg ctggaggaca gtggcacgat ctcggctcac    17580
tgcagcctct gcctcctggg tccaagcaat tctcgtgcct caacctcctg agcagatggg    17640
attacaggcg tgcaccacca tgctcatctt cttttttgtat ttttagtaga cgggggttt    17700 cgccatgttg gccaggctgg tctcgaactc ctggcctcaa gtgatccgcc cacctcggcc    17760
tcccaaagtg ctgggattac aagtgtaagc caccatgccc ggcctgtttt atcttttctt    17820
tatggtactt accacctgca ggggctttgc cgggctcatc acctgttcaa gcaacatgtc    17880
tggcacccac aagacactca gtggatttct gttgagtaaa taagtgaatt ttccctaccc    17940
aggctggggc atgaggaaga tatgagaggt atagcagaat atgacatgaa cctgggttgt    18000
ccccagaaag agagttgaag gtgaaagctc ttcatagtat cctagggttc gtgtgtgtgt    18060
gtgtgtgtgt gtgtgtgtgt gtgcatgtgc acgtgtgtgt gtatgtgtgt tcctggaaga    18120
ataggtcctg gagaaatagt cccattgctt tttccctgag aacatttcaa agtgctctct    18180
ggaagtcttg gaattctaga gaatccccca aactggccca ggcctcctta gggatccccc    18240
taacctgaat ggggttgatgg aggaatgcca ccctgagccc tggggccctc ccgacacaaa    18300
```

-continued

```
agggagggct ggtgcagaca tttcgcattt tcttcacttg aacacctctc tgctgctttt    18360
gggtggggcc atcttggcgt aggccaggtc tgaggacaaa ggtgtctctg tttggggtgc    18420
agattgcaga aggcatggcc ttcatcgagc agaggaacta catccaccga gacctccgag    18480
ctgccaacat cttggtctct gcatccctgg tgtgtaagat tgctgacttt ggcctggccc    18540
gggtcattga ggacaacgag tacacggctc gggaaggtag ggaacgctgc aagcagccc    18600 cacgttgccc atttggatgc ttgtgagtgt tgagagttga tacttgtgag agcgattggt    18660
aaaatgcaag ggactgcccc agtactagct gtgcattctt gagcttggtg gatccttctg    18720
gataatgtcc tgaacttcag agtctcactc agagattttg aggagatttt agatcagatt    18780
gagaagtact gatagatttt agagggagtg ggcaaatata tgtcgaaatt aagggtaaga    18840
gcagctttgt gcataacaga caaaaatggg gagggtatcc aaatgtccat agcaggagga    18900
tggattgtgg tatattcaca caatataata ccacgcagtg atgaaaaagc acaaactggc    18960
caggctcagt ggctcacgcc tgtaatccca gcactttagg aggccaagac tggaggactg    19020
cttgagccca gaagctcaag accagcctgg gcaacacagg aagacctagt ctctacaaaa    19080
atttaagaaa ttagccaggc atggtggcac atgcctgtat gcctgtagtt gtggctactc    19140
aggaggttag ggtgagagga tcacttgagt ctaggaagct gaagctgcag taagccatga    19200
tcatgccact gcacccagcc tggtggacag agcaagatct tgtcaaaaga aagaaaaga    19260 aaagaaaaga aagaaagaaa gaaagaaaga aagaaagaaa gaaagaaaga aagaaagaaa    19320
gaaggaaaga aagaaagaga gagaaagaga aagaaagaaa gaaagaaaga aagaaagaaa    19380
gaaagaaaga aagaaagaaa gaaagaaaga aagaaagaa agaggcacaa gccaatgcta    19440
aatgcaccaa aatgggtaac tctcacaggt ataatatcaa aatgaaagaa attagaccaa    19500
aaaaaaagag tagatgccac ttggtttcgt ttttgtgaaa ttctaaaaga gacaaaacat    19560
gtaattggac attcatggca gcattcttcc taatagccaa aaaatggaaa caacactctt    19620
taatgtccat caattgatga acagacgaac aaaatgtgat atatccatac aatggaatat    19680
tatttggcca taaaatggaa tgaagtacta cgccaggcta aacacagat gacccttaaa    19740 aacattttgt taaaggaaag ccaacatgaa gaccacatgt tgtataattc cccttctatg    19800
aaatgtccag aagaggcaat cttttttttt tctttgagat ggagtcttgc tgtcacccag    19860
gctagagtgc agtggctcaa tctcagctca ctgcaacctc tgcctcccag gttcaagcga    19920
ttcttgtgcc tcagccttct gagtagctgg gattacaggc gcacaccacc atacccagct    19980 aattttgta ttttagtag ataacagggt ttcaccatgt tggccaggct gaactcaaac    20040
tcctgacctc aagtgatccg cccgccttgg cctcccaaac tgctgggatt acaggtgtga    20100
gccaccatgc ccggcccaga acagacaaat ctaaagagac agaaagtaga ttattggtgc    20160
ctacagctgg tggtgggag ttgggagaaa tgaggagtga cttctgtggg ttttttgcag    20220
ggaaatgtga tgaaagtatt ctaaaatcca caactttgta aatattctga aagccacgga    20280
attatacact ttaaatgggt gaatgtatg gtctgtgaat tctatctcga taaagctgtt    20340
aaagaaagaa acaggcaaaa tttatttata gcactagagg tcagaattgc agtcaccttt    20400
agtttctgtt agcctaatat ttatttattt atttatttat ttatttattt atttatttat    20460
ttattttgag acggagtctc gctctgctgc ccaggctgga gtgcattggc gccatctcag    20520
ctcactgcaa actccacctc ctgggtttaa gtgattgtcc tgcctcagcc tcccaagcag    20580
ctgggattac aagcatgtgc catcatgccc agctagtttt tgtattttta gtagagacag    20640
```

```
ggtttcacca tgttggccag gctggtctcg aactgatgac ctcaagtgat tcacccacct    20700
gggcctcccg aagtgctggg attacagatg cgagccactg tgccagtcct atttattttt    20760
ttaaagagac gggtgcggcc gggcacagtg gctcacacct gtaataccag cactttggga    20820
ggccaaggca ggcggatcac aaggtcagga gtttgagacc agcctggcca atatggtgaa    20880
accctgtctc tactaaagat acaaaaatta gctgggcgtg gtggcaggtg cctgtagtcc    20940
cagctactcg ggaggctgag gcaggagaat catttgaacc cggaggcag aggttgcagc     21000 aatgagccga gattgtgcca ttgcactcca gcctgggtga tagagcgaga ctccgtctca    21060 aaaaaaaaa aaaaaaaaa agataggtgc ttgctctgtt gcccaggctg tagtggaggg      21120
gtgagatcat agctcactgt agcctccaac tcttgggctc aagcaatctt ccagcctcag    21180
cctcctgagt acctgaaact acagatacgt gctaccatgc ccagctaatt ttttaattat    21240
ttgtagagat agtgtctcac tgtgttgccc aggctggtct caaactcctg gacttacgtg    21300
atcctcctgc ctcaggctct gaaagtgcta ggattacagg catgagccac tatgcacagg    21360
ctgcagtcac cttaagtaag ggggtattaa ctggaaggac gcagaaagga gcgttctgaa    21420
atgctgaaaa tgttctacag cccaatctga tggtgattac aagggtatat atatatatat    21480
aaagctgcag caaaatggat attaaagatt tgtgcatatt atttcatgta cgttataact    21540
cgattaaaaa aaatttagac cgggcacagt ggctcatgac tataatccta gcactttggg    21600
aggccaaaat gggcagattg cttgagccca ggagttcaag accagcctgg caatatagc     21660 aagaccccat ctctacaaaa aatttaaaaa taagtcaggc gtggtggtgt gagcctgtgg    21720
tccctgctac tcaggaggct gaggcgggag aatcgcttga gcccaggagg ttgaggctgc    21780
agtgagccaa gatcatgtca ctgcactcca gcctgtgtaa cagagcaaga ctttgtctca    21840
aaaaagtaaa taaatagggc cgggcacgtt ggctcatgcc tgtaattcca gcactttggg    21900
aggctgaggt gggaggatca cgaggtcagg agatcgagac catcctggct aacacggtga    21960
aaccccatct ctactaaaaa tacaaaaaat tagccaggcg tggtggcggg cacctgtagt    22020
cccagctact gggagactg aggcaggaga atggcgtgaa agccgggagg cggaacttgc     22080
agtgagctga gatgacacca ctgcactcca gcctgggcaa acagagcgag accctgtctc    22140
aaaacataaa taaataaata aataaataaa tgtaatgact aaaggaataa aagtagaatg    22200
tataatttct aaaccagaag aagataagca ggaaatcaag aaaagtctgt agatccaaag    22260
gaggaaggga gaaaacatat acacacacac acactctcac acacacaaac acacacatag    22320
aacattttca aaacttgacc atgtactcag tcataaagca ggtctcaaca aattccaaag    22380
aacatatatt ctatagacca tgttcaccaa ccatgatata attaaactaa acactttta     22440 aaaaaggata actatgccag gtgcggtggc tcacacctat aatcccagtg ctttaggagg    22500
ccaagatggg aggatcactt gagcccagga gttttgagaa caggctgggg aacataataa    22560
aacactgtct ctacaaattt ttctattttt ttatatttta tttttttta ttttattta     22620 tttttgagac ggagtctgac tctatcatcc aggctggagt gcagtggtgt gatctcggtt    22680
cactgcaacc tccatcccct gggttcaagt gattctcctg tctcagcctg tagctggaac    22740
tacaggcacc tgccaccatg cccagctaat tttgtatttt tagtagagat ggagttggcc    22800
aggctggtct cgaattcctg acctcaggtg atcctcctcc ttggtctccc aaagtgctgg    22860
gattacaggc acaagccacc atacctggcc aaaaaattt ttttaattag cttggcataa     22920
tggggcacac ctgtaacccc aggggcttga gaggctgagg caggaggata gcttgaggtc    22980
aggagttcga ggcttcagtg aactatgatt gtgccactgc gctccagcct gggcactctg    23040
```

-continued

```
tctctaaaag aaaaaaaaaa tgaaaaggct aactaaaccc atgtcagact aggtgggagg    23100
aagggcgggt aaagggagag acacatagtg actggtggga acctcatggg ctgagagcca    23160
gaatcctccc ttttcccatc gcccaggatg agaggactga ggcatcagct gcaacctgga    23220
ctcaaggccc cctgaagtcc ttctgtcccc aaagacctgt gacctctggg attccactct    23280
tcggagttgc agttaactgg ggtatcagct gaatcaacga ggaggattct agagtgaact    23340
tccacaccat accccaggcc cctaagccca ctcctccttg tttagccatc tgtcctcagg    23400
atggatgtcc cttgcttcca cagggaggcc acgtatcagg gaaattgcag gtctgcaggg    23460
gcagatgttg gcagctcttg cccttgcctg ttccccacc ttagcagagc caaccctcac    23520
tactccccag ccttccccga ctctgctctg ttcaaccctg caggggccaa gttccccatc    23580
aagtggacag ctcctgaagc catcaacttt ggctccttca ccatcaagtc agacgtctgg    23640
tcctttggta tcctgctgat ggagatcgtc acctacggcc ggatccctta cccaggtagg    23700
gaagggcat cagctcaggg ctgctaccag ggcccagtct ggcaatgggc tcatctcaac    23760
aacatgtcca ttcaaactga gttcttgatc ctcaccccca accttccctc acctttcctg    23820
tcttagttaa aggcacctcc atccatctaa tgtcttaagc ctgaaatctg ggggcttcct    23880
tggcccttcc ttctctctca ctcctatgac ttttttttt ttttttttt ttttgagac      23940
ggagtctccc tctgtcaccc aggctggagt gcagtgacgt gatctcggct cactgcaacc    24000
tccgcctccc aggttcaagc gattctcctg cctcagcctc ctgagtaact gggattacaa    24060
gcatccacca ccatgcctgg ctaatttttg tattttagt agagacgggg tttcaccatg    24120
ttggccaggc tggtctcgaa ctgctgacct taggtgatgc gcctgcctcg gcctcccaaa    24180
gtgctgggat tacaggcgtg agccactgtg cctggcctca cccctatgac atctgagcag    24240
tcacagggtt ttggccactc gactccaaaa catatcccaa gtctcaccac tttgaaccc    24300
acagtctcca ctgcatccag gccagcgtca tctcccatag atggtgcagc ggcatcctca    24360
tcagtcttac tgctttctcc ctcctcgtcc tacagcctat tctccacttg cagccagaag    24420
gataattcta aactttaaat cagatcttgt cctttctcca ccttttttt tttttttaag    24480
acaaggtctc actctgtcac tgaggctgta gtgcagtggt gtaatcatag ctcatggcag    24540
cctcgacttc ctaggctcaa atgatcctcc cgcttcagcc tcccgagtat ctgggaccat    24600
aggcacatgc caccatgtct ggctattttt tattttttta attttttgt agagacttgg    24660
tctcactacg ttgtgcagcc tggtctctaa cttccaggct caaacgatcc tccagccttg    24720
gcctcccaaa atgctgggat tacagacaca caccaccatg cccagctaat tctttaaatt    24780
ttttgagaga caaggtattg ctatgttgcc gggctggtga tttccatttt taagcgatgc    24840
tttcagcatg gagagtgaat gggagggaaa gggaacaggg tggcagccag tgaggaggcc    24900
acagcagtgg cccaggcaga ggtgatgatg gtctggacag ggtggtggca ttcgtgactg    24960
gcatacgttg atgaactggt gctacgtttc aaaaggagaa aagatctgac ttgctgactt    25020
aggaggtgag agagagagaa taaaggatga ttaccctggc tttgcaccac agggtgggta    25080
atggtctagg gatagaaatt ggagagctct gttttagctc tgctaaattt gagttgactt    25140
aaatatagag acatccaagt aaaggaagca cttgagttca tgagtttgga gtttgagact    25200
aataatataa aattggggat cacagacatt gaatggctat tcttatgaat agctaataga    25260
aacttgaact gaacaaaaaa atggtcccac ccataggtta acattgaatc tggccacctg    25320
aatgttttgt cttgagggtg cactagtcaa aaccaggcaa cacacaatag acgctgaatc    25380
```

```
cattaggatg tgttccacag caagcaacaa aataacagac aaagagtaac tgaaatagaa   25440
gcaatctatt actcccaatc ttccattggt gactggttag ttcagcaact cagcagctgt   25500
caggactctg ggttcctgtc tctatgatgg tcttctccat gttgtcagct ccaagtatca   25560
taagtatctc acagtgttca aggaagagaa tgaagggtgc gttctccaaa gactctcctc   25620
taagcgggag gaaaaacctt tccatcactt tcccagcaga cctccccatc agctcccatt   25680
ggcccaaact gggtcccagg cccatgtcct agctgcaagt gaagctgagg gtggaagtct   25740
gtctttcaca gtggaagggg ctcagcttgc aaggtgaggt ggggagtgat gcctgctggg   25800
gaggccacag ggcctgccac ccctgggctc tcatttccca actgcttccg tttctaattc   25860
cacggctcct tttcagggat gtcaaaccct gaagtgatcc gagctctgga gcgtggatac   25920
cggatgcctc gcccagagaa ctgcccagag gagctctaca acatcatgat gcgctgctgg   25980
aaaaaccgtc cggaggagcg gccgaccttc gaatacatcc agagtgtgct ggatgacttc   26040
tacacggcca cagagagcca gtaccaacag cagccatgat agggaggacc agggcagggc   26100 caggggggtgc ccaggtggtg gctgcaaggt ggctccagca ccatccgcca gggcccacac   26160
ccccttccta ctcccagaca cccacccctcg cttcagccac agtttcctca tctgtccagt   26220
gggtaggttg gactggaaaa tctcttttg actcttgcaa tccacaatct gacattctca   26280
ggaagccccc aagttgatat ttctatttcc tggaatggtt ggattttagt tacagctgtg   26340
atttggaagg gaaactttca aaatagtgaa atgaatattt aaataaaaga tataaatgcc   26400 aaagtctttta ccaaaacgtt ggttttcctg tccttccaat tcctgaatat ctatttgcct   26460
tcttgctgta tgacaagtca gaaatggtga aggactctcc cggggaccag aaatacaaag   26520
acaagtgggg ttcagactgg gtgctgtggc tcccacctat aataccagtg ctttgggaga   26580
ccgaggagcg ggggattgct tgagcccagg aggtcgaggc cacagtgagc tatgatcgtg   26640
ccactgcact ctagcctgag cgacacagtg agaccctgtt taaaaaaaa aaaaaaagat   26700 gaagaagaag aaagaaagga aaggaaagaa aattgggggtt caatgcttga ggttttctaa   26760
ctgccctaaa atagttactg gctatattag tttcctcttg ctcctgtaac aaattaccac   26820
atatctggta gcttaagaca acaaaactgc ataacattac ttggccgggc ataatggctc   26880
atgcctatag ttccagcatt ttgggagact gaggtgggtg atcacttgag atcaggagtt   26940
cgagaccagc ctggccaaca tggtgaaacc ccgtctctac taaaaataca aaaattagcc   27000
aggcatggtg gtgggcgcct gtaatcctag ctactggaga ggatgaggca ggagaattgc   27060
ttgaacccgg gaggtggagg ttgcagtgag ccgagattgt accactgcac tccagcctgg   27120
gcaagacagc gagaccctgt ctcaatacat acatacatac atacatacat gtataacctt   27180
actgttccag aaaagcaaga ccctgtctca atcaatcaat caatcaatca gtcaatacat   27240
gtataacctt actgttccag aagtcagagg gactgaaatg ggttggcagg gctgcattct   27300
ttttggaggc tctaggggat aatttgtttc cttgcctttc ccagtttcta gaggctgctc   27360
ctattccttc actcatcagc ccctttcgtt cattactcca aactttgctt tcatcttcat   27420
atctcctctg agtcttcttc ccctctttta tttgtaagaa ctccttggac ccacctggat   27480
aattcagaat aatcttctca tctcaggatt cttaatcacc tttgcaaagt cccttttgcc   27540
atgtgaggta acattttcac acgctctgag ggttaggaca tgaacatctt tcgacggggg   27600 gcactttttct gccttctcca ctggtatcca gatgctggat gggttttgcc tccaaggaga   27660
tgggtcttcc aggatgacag gaatggtttc tcatgatctg ggaccctgac tttcctgtta   27720
ggccacattg ctataagagc tggtcagttt acagctcccc agagctgggg gctgcctgca   27780
```

```
                                      -continued gacctgacgt tcccatgggg tcaagcagcc atcatacttg tcgaagtggt atttgccatt   27840
gcaggaatcc tggtctggag atatggctgc tgagaggtgt ctagtaccct acaggggaag   27900
ctctcagtgg aggggtggga gacctgcgta ggaagcagag aagacgaagc agtgcgggct   27960
tcctgaatgt tgcctcagct gaaagaccct ggcagctagt ttttatcata gagagaaaga   28020
caaaagaggt ggacaatggg tgaaaacgaa acaccacctt tctatattat tgcatcccct   28080
gaaggttgta catcacatca ccccccaggg tcccatggaa tcctatacta acttgattct   28140
gtacttctga gtagggtggg gttctaacct taggaactga atataagaac agtgaaaat    28200 aaagctagca gtgtttcaat ttacctagtt ggtaatttct ttcttgcttt ctagtttggg   28260
gtatggcttg ggtacatgaa agcagagccc agggtcttct gatggaaatg ttcccttatg   28320
atttgtgata ataatccaat gggaggagta catttccctg ctccatcagt gttgagcttg   28380
accgtgagac ttgctttagc caatgggatg ttagcagatg tgatgcaagc agaggcttga   28440
aacgtgcttg tggggctggg cttgccttcc agtcttttgc cctgaaaaga acatggtccg   28500
aggaagatga gtgacagatg gagcagacct agaccaacct gcaggcctga gcccagccta   28560
gatcaactga gctccatctg acctgtggac atgtgagaga gaaatagatg cttttgtgtt   28620
ctggggttgt tttgttacat aaaagtatga cagccacagc aactgaggca cgatctcagg   28680
agttggagcc tattgcttat gaacaaggtt aagagatcaa tttctgcttc ttactctttc   28740
aatttatacc gcccaaacca acactgattt gtctctctgg tcaccgaaaa gacaggtaaa   28800
aacatgggga tagatacaac accaaaagca tgatccacaa agaaaaaaa agataaactg    28860 tacctctttta aaattaaaaa ctctgctctg ccaaagacac tattaagaaa atagaaacat   28920
ggccaagcgt ggtggctcac gcctgcaatc ccagaacttt gggaggtcga ggtgggtgaa   28980
tcaccagagg tcaggaattc gagaccagcc tggccaacat ggtaaaaccc tgtctcaact   29040
aaaaatacaa aaattagcca ggcatggtgg cgggcgcctg taatcccagc tactcgggag   29100
gctgaggcag gagaattgct tgaacccagg aggcggaggt tgcaatgagc caagatcaca   29160
ccattgcact ccagtctggg tgacaagagc aaacctctgt cttaaaaaaa aaaaaaaga   29220 aaagaaaaa agaaaagaaa agaaaagaaa aatgtgattc ccaagcttgt agaaaatatt   29280
tgcaaaagat atctctgatg aaggactggt atctgcaata tataagaac tcttaaaacc    29340 caacaattaa aaaaaccgt atctgctaaa atagctgaga ttcaaaacac tgatgacacc    29400
agatgctgag gaggatgtgg agcaacagga actctcattc attgctggtg ggaatgcaca   29460
acggtacagc cactttggaa ggcatctggc agtttattac caaactaagc ataacctact   29520
acacaatcca gcaattgtgc tcccatatga gttgaaaact tacgtctaca cacactcaca   29580
aaaatggcac atggatattt acagcagctt tattcataaa tgccaaaact tggaaacaat   29640
taagatgtcc ttcaataggt gaatggataa acaacttgtg gtatattcac ataatgggat   29700
attattcagc actaagaaaa aagagttgac caggtgcagg tgcagtggct cacacctata   29760
atcccagcac tttgggaggc taaggtggga ggattgtttg agcccagaag tttgagacca   29820
gcttgggcaa caagtgggac ccccccccccc accatatcta caaagagtta acatttagc    29880 tggttgtggt ggcatgcaac tgtggtccca gctacacagg aggctgaggc aggagaaaca   29940
cttgagccca ggagattgag gttgcagtga gccgtgattg taccactgca ctccagcctg   30000
```

<210> SEQ ID NO 11
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 11
tcgtcatcgt cttcatctcc                                               20

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
cctcagagcc atcgtcgtca                                               20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
cctgaggtcc cctcagagcc                                               20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
cagcccggat cctcgcagct                                               20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
gggcagcccg gatcctcgca                                               20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
tggatgtggg atccggcacg                                               20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
tggctattag gccccggctt                                               20
```

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
atgtcctcag agcctgcctc                                           20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
ttctggaagc tgaggtcttc                                           20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
cccttctgga agctgaggtc                                           20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
tagccctcct tccgggtggc                                           20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ctgatgccct tgaaaaacca                                           20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
gcccagcatg ttgccgggag                                           20

<210> SEQ ID NO 24
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 24
aaggagccca gcatgttgcc					20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
atgaaggagc ccagcatgtt					20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
gatcatgaag gagcccagca					20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
ccggatcatg aaggagccca					20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
cggacaaaga gtagcttcct					20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
cagggtccgg atcttgtaat					20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
tcgttcccct tcttgtagtg					20

```
<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gacagtttct ggcagagccc                                          20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
gacatgcagg gcaccgacag                                          20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
ggcttggaag acatgcaggg                                          20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
agctccaagt ttcttctcca                                          20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
cccagctcca agtttcttct                                          20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ctgcccagct ccaagtttct                                          20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 37
ggtggccatc cagacttccc                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
ttgttgtagg tggccatcca                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tgtgcttgtt gtaggtggcc                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
tggtgtgctt gttgtaggtg                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
gacatgctcc ctggcttcat                                              20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ggaaggcctc caccgacatg                                              20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
gctgcagagt tttcatcacg                                              20

<210> SEQ ID NO 44
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 44
aagtttgacc agcttgtcat                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
ctccgtgatg atgtagatgg                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
catcactttt cagaaagtcc                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
ctgcttgctg ccctcatcac                                               20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ggctgagaag tcaatgagtt                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
cttctgcaat ctgggctgag                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
```
tgccttctgc aatctgggct                                              20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
aggccatgcc ttctgcaatc                                              20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
tgctcgatga aggccatgcc                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
tagttcctct gctcgatgaa                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
tcggtggatg tagttcctct                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
tcagcaatct tacacaccag                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
gacccgggcc aggccaaagt                                              20

<210> SEQ ID NO 57
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 57
tcgttgtcct caatgacccg                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
aacttggccc cttcccgagc                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
gcttcaggag ctgtccactt                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tctgacttga tggtgaagga                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
gggatccggc cgtaggtgac                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
ggtttgacat ccctgggtaa                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
catccggtat ccacgctcca                                               20
```

```
<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
gcgcatcatg atgttgtaga                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
agcacactct ggatgtattc                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tccagcacac tctggatgta                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
tcatccagca cactctggat                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
atggctgctg ttggtactgg                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
cctccctatc atggctgctg                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 70
ccttcgagcc accacctggg                                                        20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
cagtccaacc tacccactgg                                                        20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ggattgcaag agtcaaaaag                                                        20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
gtcagattgt ggattgcaag                                                        20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
cctgagaatg tcagattgtg                                                        20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
gctgtaacta aaatccaacc                                                        20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
acagctgtaa ctaaaatcca                                                        20

<210> SEQ ID NO 77
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
actattttga aagtttccct                                                    20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
tcatttcact attttgaaag                                                    20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
taagacttgc atttatatct                                                    20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
agatgtgcac caccatgctt                                                    20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tgcaccaccc tatattatca                                                    20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
aacatacata ttaggctggt                                                    20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
```

```
gagtagcttc ctgaattgac                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
tcgttcccct ctggaacaga                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
gggtccttac ccatccagac                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
ggccagcaga agatgccaca                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
tttgacatcc ctgaaaagga                                               20
```

ANTISENSE MODULATION OF HEMATOPOIETIC CELL PROTEIN TYROSINE KINASE EXPRESSION

FIELD OF THE INVENTION

The present invention provides compositions and methods for modulating the expression of hematopoietic cell protein tyrosine kinase. In particular, this invention relates to compounds, particularly oligonucleotides, specifically hybridizable with nucleic acids encoding hematopoietic cell protein tyrosine kinase. Such compounds have been shown to modulate the expression of hematopoietic cell protein tyrosine kinase.

BACKGROUND OF THE INVENTION

Cells in higher animals normally divide only when they are stimulated by growth factors produced by other cells and act by binding to receptor tyrosine kinases on dividing cells. Cancer cells proliferate excessively because, as a result of accumulated mutations, they are able to divide without stimulation from other cells and therefore are no longer subject to normal controls on cell proliferation. The mutated genes which lead to excessive proliferation were originally called oncogenes before their origin as normal genes was understood. The normal genes, from which they arise, are thus often referred to as proto-oncogenes.

The cellular src gene was the first molecularly-defined proto-oncogene and its product, Src, is now known to be the source of the first detected tyrosine phosphorylation event. Mutations in the src gene, captured in the genome of Rous sarcoma virus, gave rise to the prototype oncogene v-src. Since the first descriptions of the protein tyrosine kinase activity of v-Src, many other proto-oncogenes have been described (Brown and Cooper, *Biochim. Biophys. Acta.*, 1996, 1287, 121–149).

Intracellular tyrosine kinases can now be divided into at least 8 subfamilies based on catalytic domain sequence similarity and the presence or absence of other functional domains. The members of the Src family in vertebrates include Src, Fyn, Yes, Fgr, Hck, Lck, Blk and Yrk (Brown and Cooper, *Biochim. Biophys. Acta.*, 1996, 1287, 121–149).

Hematopoietic cell protein tyrosine kinase (also known as Hck and JTK9) was first cloned in 1987 (Quintrell et al., *Mol. Cell Biol.*, 1987, 7, 2267–2275; Ziegler et al., *Mol. Cell Biol.*, 1987, 7, 2276–2285) and later mapped to chromosome 20q11–q12. The hematopoietic cell protein tyrosine kinase gene has been shown to encode two isoforms, $p59^{Hck}$ and $p61^{Hck}$ which are derived from a single mRNA by alternative initiation of translation (Robbins et al., *Mol. Cell Biol.*, 1995, 15, 3507–3515).

Hematopoietic cell protein tyrosine kinase expression is highest in differentiated monocytic and granulocytic cells, suggesting that the protein might function in myeloid differentiation or activation (Lichtenberg et al., *Oncogene*, 1992, 7, 849–858). Taguchi et al. have demonstrated that hematopoietic cell protein tyrosine kinase and Lyn are the major Src-family protein tyrosine kinases expressed in precursor lymphoblastic leukemia cells, the cell type from which childhood leukemia arises most frequently (Taguchi et al., *Exp. Hematol.* (N.Y.), 2000, 28, 55–64).

Cartledge et al. have recently generated monoclonal antibodies to murine hematopoietic cell protein tyrosine kinase for the purpose of pursuing investigations of the roles of hematopoietic cell protein tyrosine kinase in signal transduction (Cartledge et al., *Hybridoma*, 2000, 19, 323–330)

Hematopoietic cell protein tyrosine kinase has been demonstrated to interact with Bcr-Abl, a constitutively active protein tyrosine kinase expressed as a result of the Philadelphia translocation in chronic myelogenous leukemia. Kinase-defective hematopoietic cell protein tyrosine kinase was found to suppress Bcr-Abl-induced outgrowth of the cytokine-dependent myeloid leukemia cell line (Lionberger et al., *J. Biol. Chem.*, 2000, 275, 18581–18585).

Investigations of polymorphonuclear neutrophils isolated from mice deficient in hematopoietic cell protein tyrosine kinase and Fgr have identified a role for these Src family kinases in a signaling pathway leading to granule-plasma membrane fusion and have identified Fgr and hematopoietic cell protein tyrosine kinase as potential targets for pharmacological control of the inflammatory process (Mocsai et al., *J. Immunol.*, 1999, 162, 1120–1126).

Investigations of encephalomyocarditis virus-infected mice treated with the Src kinase inhibitor PP2 have indicated that hematopoietic cell protein tyrosine kinase plays an important role in the activation of macrophages and the subsequent production of tumor necrosis factor-alpha and nitric oxide which lead to the destruction of pancreatic beta cells, leading to diabetes. The inhibition of hematopoietic cell protein tyrosine kinase was found to prevent the onset of diabetes in this study (Choi et al., *J. Virol.*, 2001, 75, 1949–1957).

Hematopoietic cell protein tyrosine kinase and Fgr double knock-out mice have been found to be resistant to endotoxic shock and exhibit reduced neutrophil migration, indicating that hematopoietic cell protein tyrosine kinase may be an appropriate target for therapeutic intervention in inflammatory diseases (Lowell and Berton, *Proc. Natl. Acad. Sci. U.S.A.*, 1998, 95, 7580–7584).

Tokunaga et al. have reported inhibition of human immunodeficiency virus type 1 (HIV-1) infectivity by the expression of a dominant-negative hematopoietic cell protein tyrosine kinase protein in T293 cells, indicating a role of Src kinases in regulation of entry of HIV-1 into target cells (Tokunaga et al., *J. Virol.*, 1998, 72, 6257–6259).

Small molecule inhibitors of Src family tyrosine kinases are well known in the art. Examples include natural products such as radiciol and geldanamycin, ring-fused pyrimidines, benzopyrans and thiol-reactive agents (Showalter and Kraker, *Pharmacol. Ther.*, 1997, 76, 55–71).

Schindler et al. have reported the crystal structure of hematopoietic cell protein tyrosine kinase in complex with a pyrazolo pyrimidine-type Src family kinase inhibitor known as PP1 (Schindler et al., *Mol. Cell*, 1999, 3, 639–648).

A 21-mer antisense phosphorothioate oligonucleotide targeting the seven codons immediately downstream from the translation initiation site of the murine hematopoietic cell protein tyrosine kinase gene has been used to inhibit hematopoietic cell protein tyrosine kinase expression in investigations of tumor necrosis factor production by murine macrophages (English et al., *J. Exp. Med.*, 1993, 178, 1017–1022) and lipopolysaccharide and interferon-gamma-mediated phosphorylation of the proto-oncogene vav (English et al., *J. Leukocyte Biol.*, 1997, 62, 859–864).

A 20-mer phosphorothioate oligonucleotide targeting the start codon of human hematopoietic cell protein tyrosine kinase was used to inhibit hematopoietic cell protein tyrosine kinase in investigations of neutrophil apoptosis stimulated by granulocyte-macrophage colony-stimulating factor (Wei et al., *J. Immunol.*, 1996, 157, 5155–5162).

Currently, there are no known therapeutic agents that effectively inhibit the synthesis of hematopoietic cell protein tyrosine kinase. To date, investigative strategies aimed at modulating hematopoietic cell protein tyrosine kinase expression have involved the use of antibodies, small molecule inhibitors and antisense oligonucleotides. Consequently, there remains a long felt need for additional agents capable of effectively inhibiting hematopoietic cell protein tyrosine kinase function.

Antisense technology is emerging as an effective means for reducing the expression of specific gene products and may therefore prove to be uniquely useful in a number of therapeutic, diagnostic, and research applications for the modulation of expression of hematopoietic cell protein tyrosine kinase.

The present invention provides compositions and methods for modulating expression of hematopoietic cell protein tyrosine kinase.

SUMMARY OF THE INVENTION

The present invention is directed to compounds, particularly antisense oligonucleotides, which are targeted to a nucleic acid encoding hematopoietic cell protein tyrosine kinase, and which modulate the expression of hematopoietic cell protein tyrosine kinase. Pharmaceutical and other compositions comprising the compounds of the invention are also provided. Further provided are methods of modulating the expression of hematopoietic cell protein tyrosine kinase in cells or tissues comprising contacting said cells or tissues with one or more of the antisense compounds or compositions of the invention. Further provided are methods of treating an animal, particularly a human, suspected of having or being prone to a disease or condition associated with expression of hematopoietic cell protein tyrosine kinase by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding hematopoietic cell protein tyrosine kinase, ultimately modulating the amount of hematopoietic cell protein tyrosine kinase produced. This is accomplished by providing antisense compounds which specifically hybridize with one or more nucleic acids encoding hematopoietic cell protein tyrosine kinase. As used herein, the terms "target nucleic acid" and "nucleic acid encoding hematopoietic cell protein tyrosine kinase" encompass DNA encoding hematopoietic cell protein tyrosine kinase, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of hematopoietic cell protein tyrosine kinase. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding hematopoietic cell protein tyrosine kinase. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding hematopoietic cell protein tyrosine kinase, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in (To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'–5' linkages, 2'–5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$) —$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, S$CH_3$, OCN, Cl, Br, CN, $CF_3$, O$CF_3$, SO$CH_3$, $SO_2CH_3$, $ONO_2$, $NO_2$, $N_3$, $NH_2$, heterocycloalkyl, heterocycloalkaryl, aminoalkylamino, poly-alkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethylamino-ethoxyethyl or 2'-DMAEOE), i.e., 2'-O—$CH_2$—O—$CH_2$—N($CH_3$)$_2$, also described in examples hereinbelow.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b] [1,4]benzothiazin-2(3H)-one), G-clamps such as a substituted phenoxazine cytidine (e.g. 9-(2-aminoethoxy)-H-pyrimido[5,4-b] [1,4] benzoxazin-2(3H)-one), carbazole cytidine (2H-pyrimido[4,5-b] indol-2-one), pyridoindole cytidine (H-pyrido[3',2':4,5] pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos.: 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos.: 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression.

Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos.: 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like;

(c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of hematopoietic cell protein tyrosine kinase is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding hematopoietic cell protein tyrosine kinase, enabling sandwich and other assays to easily be constructed to exploit this fact. Hybridization of the antisense oligonucleotides of the invention with a nucleic acid encoding hematopoietic cell protein tyrosine kinase can be detected by means known in the art. Such means may include conjugation of an enzyme to the oligonucleotide, radiolabelling of the oligonucleotide or any other suitable detection means. Kits using such detection means for detecting the level of hematopoietic cell protein tyrosine kinase in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylamino-methylethylene P(TDAE), polyaminostyrene (e.g. p-amino), poly (methylcyanoacrylate), poly(ethylcyanoacrylate), poly (butylcyanoacrylate), poly(isobutylcyanoacrylate), poly (isohexylcynaoacrylate), DEAE-methacrylate, DEAE-hexylacrylate, DEAE-acrylamide, DEAE-albumin and DEAE-dextran, polymethylacrylate, polyhexylacrylate, poly(D, L-lactic acid), poly(DL-lactic-co-glycolic acid (PLGA), alginate, and polyethyleneglycol (PEG). Oral formulations for oligonucleotides and their preparation are described in detail in U.S. applications Ser. Nos. 08/886,829 (filed Jul. 1, 1997), 09/108,673 (filed Jul. 1, 1998), 09/256,515 (filed Feb. 23, 1999), 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.,* 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms,* Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ (glyceryl dilaurate/cholesterol/polyoxyethylene-10-stearyl ether) and Novasome™ II (glyceryl disterate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. Nos. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, Critical Reviews in Therapeutic Drug Carrier Systems, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy,* 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1
Nucleoside Phosphoramidites for Oligonucleotide Synthesis
Deoxy and 2'-Alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-methoxyethyl) Modified Amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L).

The insoluble salts were filtered, washed with acetone (150 mL) and the filtrate evaporated. The residue (280 g) was dissolved in CH$_3$CN (600 mL) and evaporated. A silica gel column (3 kg) was packed in CH$_2$Cl$_2$/acetone/MeOH (20:5:3) containing 0.5% Et$_3$NH. The residue was dissolved in CH$_2$Cl$_2$ (250 mL) and adsorbed onto silica (150 g) prior to loading onto the column. The product was eluted with the packing solvent to give 160 g (63%) of product. Additional material was obtained by reworking impure fractions.

2'-O-methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with CH$_3$CN (200 mL). The residue was dissolved in CHCl$_3$ (1.5 L) and extracted with 2×500 mL of saturated NaHCO$_3$ and 2×500 mL of saturated NaCl. The organic phase was dried over Na$_2$SO$_4$, filtered and evaporated. 275 g of residue was obtained. The residue was purified on a 3.5 kg silica gel column, packed and eluted with EtOAc/hexane/acetone (5:5:1) containing 0.5% Et$_3$NH. The pure fractions were evaporated to give 164 g of product. Approximately 20 g additional was obtained from the impure fractions to give a total yield of 183 g (57%).

3'-O-acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in CHCl$_3$ (800 mL) and extracted with 2×200 mL of saturated sodium bicarbonate and 2×200 mL of saturated NaCl. The water layers were back extracted with 200 mL of CHCl$_3$. The combined organics were dried with sodium sulfate and evaporated to give 122 g of residue (approx. 90% product). The residue was purified on a 3.5 kg silica gel column and eluted using EtOAc/hexane (4:1). Pure product fractions were evaporated to yield 96 g (84%). An additional 1.5 g was recovered from later fractions.

3'-O-acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-methoxyethyl-5'-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with NH$_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-benzoyl-2'-O-methoxyethyl-5'-O-dimethoxytrityl-5-methylcytidine-3'-amidite

N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl) phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) Nucleoside Amidites and 2'-O-(Dimethylaminooxyethyl) Nucleoside Amidites 2'-(Dimethylaminooxyethoxy) Nucleoside Amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10° C. to 0° C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-butyldiphenylsilyl-2'-O-[N,N-dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'- dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) Nucleoside Amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl) guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl) guanosine and 2-N-isobutyryl-6-O-diphenylcarbamoyl-2'-O-(2-ethylacetyl)-5'-O-(4,4'-dimethoxytrityl) guanosine which may be reduced to provide 2-N-isobutyryl-6-O-diphenylcarbamoyl-2'-O-(2-hydroxyethyl)-5'-O-(4,4'-dimethoxytrityl) guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-([2-phthalmidoxy]ethyl)-5'-O-(4,4'-dimethoxytrityl) guanosine-3'-[(2-cyanoethyl)-N,N-diisopropylphosphoramidite].

2'-Dimethylaminoethoxyethoxy (2'-DMAEOE) Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. $O^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy) Ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with $CH_2Cl_2$ (2×200 mL). The combined $CH_2Cl_2$ layers are washed with saturated $NaHCO_3$ solution, followed by saturated NaCl solution and dried over anhydrous sodium sulfate. Evaporation of the solvent followed by silica gel chromatography using MeOH:$CH_2Cl_2$:$Et_3N$ (20:1, v/v, with 1% triethylamine) gives the title compound.

5'-O-dimethoxytrityl-2'-O-[2(2-N,N-dimethylaminoethoxy)-ethyl)]-5-methyl uridine-3'-O-(cyanoethyl-N,N-diisopropyl) phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference. 3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethyl-hydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-O-phosphor-amidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-O-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-methoxyethyl)]-[2'-deoxy]-[2'-O-(methoxyethyl)] Chimeric Phosphorothioate Oligonucleotides

[2'-O-(2-methoxyethyl)]—[2'-deoxy]—[-21-O-(methoxy-ethyl)] chimeric phosphorothioate oligonucleotides were prepared as per the procedure above for the 2'-O-methyl chimeric oligonucleotide, with the substitution of 2'-0-(methoxyethyl) amidites for the 2'-O-methyl amidites.

[2'-O-(2-methoxyethyl) Phosphodiester]-[2'-deoxy Phosphorothioate]-[2'-O-(2-methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methylamidites, oxidization with iodine to generate the phosphodiester internucleotide linkages within the wing portions of the chimeric structures and sulfurization utilizing 3, H-1,2 benzodithiole-3-one 1, 1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6
Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by 31P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7
Oligonucleotide Synthesis—96 Well Plate Format

Oligonucleotides were synthesized via solid phase P (III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3, H-1,2 benzodithiole-3-one 1, 1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8
Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9
Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 4 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum ((Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

Treatment With Antisense Compounds:

When cells reached 70% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10
Analysis of Oligonucleotide Inhibition of Hematopoietic Cell Protein Tyrosine Kinase Expression Antisense modulation of hematopoietic cell protein tyrosine kinase expression can be assayed in a variety of ways known in the art. For example, hematopoietic cell protein tyrosine kinase mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. The preferred method of RNA analysis of the present invention is the use of total cellular RNA as described in other examples herein. Methods of RNA isolation are taught in, for example, Ausubel, F. M. et al., Current Protocols in Molecular Biology, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., Current Protocols in Molecular Biology, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of hematopoietic cell protein tyrosine kinase can be quantitated in a variety of ways well known in the art, such as immunoprecipitation, Western blot analysis (immunoblotting), ELISA or fluorescence-activated cell sorting (FACS). Antibodies directed to hematopoietic cell protein tyrosine kinase can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1–11.12.9, John Wiley & Sons, Inc., 1997. Preparation of monoclonal antibodies is taught in, for example, Ausubel, F. M. et al., Current Protocols in Molecular Biology, Volume 2, pp. 11.4.1–11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1–10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1–11.2.22, John Wiley & Sons, Inc., 1991.

Example 11
Poly(A)+mRNA Isolation

Poly(A)+mRNA was isolated according to Miura et al., Clin. Chem., 1996, 42, 1758–1764. Other methods for poly(A)+mRNA isolation are taught in, for example, Ausubel, F. M. et al., Current Protocols in Molecular Biology, Volume 1, pp. 4.5.1–4.5.3, John Wiley & Sons, Inc., 1993. Briefly, for cells grown on 96-well plates, growth medium was removed from the cells and each well was washed with 200 μL cold PBS. 60 μL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 μL of lysate was transferred to Oligo d (T) coated 96-well plates (AGCT Inc., Irvine Calif.). Plates were incubated for 60 minutes at room temperature, washed 3 times with 200 μL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 μL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12
Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 μL cold PBS. 150 μL Buffer RLT was added to each well and the plate vigorously agitated for 20 seconds. 150 μL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 μL of Buffer RW1 was added to each well of the RNEASY 96™ plate and incubated for 15 minutes and the vacuum was again applied for 1 minute. An additional 500 μL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 170 μL water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13
Real-time Quantitative PCR Analysis of Hematopoietic Cell Protein Tyrosine Kinase mRNA Levels Quantitation of hematopoietic cell protein tyrosine kinase mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM, obtained from either Operon Technologies Inc., Alameda, Calif. or Integrated DNA Technologies Inc., Coralville, Iowa) is attached to the 5' end of the probe and a quencher dye (e.g., TAMRA, obtained from either Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen, Carlsbad, Calif. RT-PCR reactions were carried out by adding 20 µL PCR cocktail (2.5× PCR buffer (—MgCl2), 6.6 mM MgCl2, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96 well plates containing 30 µL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, Analytical Biochemistry, 1998, 265, 368–374.

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 480 nm and emission at 520 nm.

Probes and primers to human hematopoietic cell protein tyrosine kinase were designed to hybridize to a human hematopoietic cell protein tyrosine kinase sequence, using published sequence information (GenBank accession number M16591.1, incorporated herein as SEQ ID NO:3). For human hematopoietic cell protein tyrosine kinase the PCR primers were:

forward primer: TTTGTCCGTGCGAGACTACG (SEQ ID NO: 4)

reverse primer: TTGTCCAGGGTCCGGATCT (SEQ ID NO: 5) and the

PCR probe was: FAM-CTCGGCAGGGAGATACCGTGAAACATTAC-TAMRA (SEQ ID NO: 6) where FAM (PE-Applied Biosystems, Foster City, Calif.) is the fluorescent reporter dye) and TAMPA (PE-Applied Biosystems, Foster City, Calif.) is the quencher dye. For human GAPDH the PCR primers were:

forward primer: GAAGGTGAAGGTCGGAGTC(SEQ ID NO:7)

reverse primer: GAAGATGGTGATGGGATTTC (SEQ ID NO:8) and the

PCR probe was: 5' JOE-CAAGCTTCCCGTTCTCAGCC-TAMRA 3' (SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Example 14
Northern Blot Analysis of Hematopoietic Cell Protein Tyrosine Kinase mRNA Levels Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human hematopoietic cell protein tyrosine kinase, a human hematopoietic cell protein tyrosine kinase specific probe was prepared by PCR using the forward primer TTTGTCCGTGCGAGACTACG (SEQ ID NO: 4) and the reverse primer TTGTCCAGGGTCCGGATCT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15
Antisense Inhibition of Human Hematopoietic Cell Protein Tyrosine Kinase Expression by Chimeric Phosphorothioate Oligonucleotides Having 2'-MOE Wings and a Deoxy Gap In accordance with the present invention, a series of oligonucleotides were designed to target different regions of the human hematopoietic cell protein tyrosine kinase RNA, using published sequences (GenBank accession number M16591.1, incorporated herein as SEQ ID NO: 3, and residues 1–30000 of GenBank accession number AL049539.2, representing a partial genomics sequence of hematopoietic cell protein tyrosine kinase, incorporated herein as SEQ ID NO: 10). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl ($2'$-MOE) nucleotides. The internucleoside (backbone) linkages are phosphorothioate (P=S) throughout the oligonucleotide. All cytidine residues are 5-methylcytidines. The compounds were analyzed for their effect on human hematopoietic cell protein tyrosine kinase mRNA levels by quantitative real-time PCR as described in other examples herein. Data are averages from two experiments. If present, "N.D." indicates "no data".

TABLE 1

Inhibition of human hematopoietic cell protein tyrosine kinase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 150717 | 5'UTR | 3 | 53 | tcgtcatcgtcttcatctcc | 0 | 11 |
| 150718 | 5'UTR | 3 | 67 | cctcagagccatcgtcgtca | 6 | 12 |
| 150719 | 5'UTR | 3 | 77 | cctgaggtcccctcagagcc | 31 | 13 |
| 150720 | 5'UTR | 3 | 122 | cagcccggatcctcgcagct | 15 | 14 |
| 150721 | 5'UTR | 3 | 125 | gggcagcccggatcctcgca | 9 | 15 |
| 150723 | Coding | 3 | 258 | tggatgtgggatccggcacg | 0 | 16 |
| 150724 | Coding | 3 | 283 | tggctattaggccccggctt | 22 | 17 |
| 150725 | Coding | 3 | 328 | atgtcctcagagcctgcctc | 72 | 18 |
| 150726 | Coding | 3 | 388 | ttctggaagctgaggtcttc | 31 | 19 |
| 150727 | Coding | 3 | 391 | cccttctggaagctgaggtc | 19 | 20 |
| 150728 | Coding | 3 | 466 | tagccctccttccgggtggc | 0 | 21 |
| 150729 | Coding | 3 | 535 | ctgatgcccttgaaaaacca | 28 | 22 |
| 150730 | Coding | 3 | 584 | gcccagcatgttgccgggag | 3 | 23 |
| 150731 | Coding | 3 | 589 | aaggagcccagcatgttgcc | 0 | 24 |
| 150732 | Coding | 3 | 592 | atgaaggagcccagcatgtt | 0 | 25 |
| 150733 | Coding | 3 | 596 | gatcatgaaggagcccagca | 0 | 26 |
| 150734 | Coding | 3 | 599 | ccggatcatgaaggagccca | 0 | 27 |
| 150735 | Coding | 3 | 636 | cggacaaagagtagcttcct | 0 | 28 |
| 150736 | Coding | 3 | 695 | cagggtccggatcttgtaat | 6 | 29 |
| 150737 | Coding | 3 | 778 | tcgttcccttcttgtagtg | 0 | 30 |
| 150738 | Coding | 3 | 799 | gacagtttctggcagagccc | 28 | 31 |
| 150739 | Coding | 3 | 814 | gacatgcagggcaccgacag | 27 | 32 |
| 150740 | Coding | 3 | 823 | ggcttggaagacatgcaggg | 19 | 33 |
| 150741 | Coding | 3 | 896 | agctccaagtttcttctcca | 21 | 34 |
| 150742 | Coding | 3 | 899 | cccagctccaagtttcttct | 19 | 35 |
| 150743 | Coding | 3 | 902 | ctgcccagctccaagtttct | 45 | 36 |
| 150744 | Coding | 3 | 926 | ggtggccatccagacttccc | 27 | 37 |
| 150745 | Coding | 3 | 934 | ttgttgtaggtggccatcca | 11 | 38 |

TABLE 1-continued

Inhibition of human hematopoietic cell protein tyrosine
kinase mRNA levels by chimeric phosphorothioate
oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 150746 | Coding | 3 | 939 | tgtgcttgttgtaggtggcc | 26 | 39 |
| 150747 | Coding | 3 | 942 | tggtgtgcttgttgtaggtg | 28 | 40 |
| 150748 | Coding | 3 | 979 | gacatgctccctggcttcat | 7 | 41 |
| 150749 | Coding | 3 | 993 | ggaaggcctccaccgacatg | 40 | 42 |
| 150750 | Coding | 3 | 1026 | gctgcagagttttcatcacg | 4 | 43 |
| 150751 | Coding | 3 | 1046 | aagtttgaccagcttgtcat | 6 | 44 |
| 150752 | Coding | 3 | 1088 | ctccgtgatgatgtagatgg | 5 | 45 |
| 150753 | Coding | 3 | 1131 | catcacttttcagaaagtcc | 7 | 46 |
| 150754 | Coding | 3 | 1145 | ctgcttgctgccctcatcac | 63 | 47 |
| 150755 | Coding | 3 | 1175 | ggctgagaagtcaatgagtt | 0 | 48 |
| 150756 | Coding | 3 | 1188 | cttctgcaatctgggctgag | 6 | 49 |
| 150757 | Coding | 3 | 1191 | tgccttctgcaatctgggct | 6 | 50 |
| 150758 | Coding | 3 | 1197 | aggccatgccttctgcaatc | 49 | 51 |
| 150759 | Coding | 3 | 1207 | tgctcgatgaaggccatgcc | 16 | 52 |
| 150760 | Coding | 3 | 1216 | tagttcctctgctcgatgaa | 36 | 53 |
| 150761 | Coding | 3 | 1226 | tcggtggatgtagttcctct | 0 | 54 |
| 150762 | Coding | 3 | 1282 | tcagcaatcttacacaccag | 0 | 55 |
| 150763 | Coding | 3 | 1301 | gacccgggccaggccaaagt | 0 | 56 |
| 150764 | Coding | 3 | 1315 | tcgttgtcctcaatgacccg | 25 | 57 |
| 150765 | Coding | 3 | 1342 | aacttggccccttcccgagc | 26 | 58 |
| 150766 | Coding | 3 | 1369 | gcttcaggagctgtccactt | 0 | 59 |
| 150767 | Coding | 3 | 1402 | tctgacttgatggtgaagga | 21 | 60 |
| 150768 | Coding | 3 | 1456 | gggatccggccgtaggtgac | 0 | 61 |
| 150769 | Coding | 3 | 1476 | ggtttgacatccctgggtaa | 3 | 62 |
| 150770 | Coding | 3 | 1514 | catccggtatccacgctcca | 20 | 63 |
| 150771 | Coding | 3 | 1562 | gcgcatcatgatgttgtaga | 2 | 64 |
| 150772 | Coding | 3 | 1618 | agcacactctggatgtattc | 9 | 65 |
| 150773 | Coding | 3 | 1621 | tccagcacactctggatgta | 19 | 66 |
| 150774 | Coding | 3 | 1624 | tcatccagcacactctggat | 43 | 67 |
| 150775 | Coding | 3 | 1665 | atggctgctgttggtactgg | 28 | 68 |
| 150776 | Stop Codon | 3 | 1675 | cctccctatcatggctgctg | 19 | 69 |
| 150777 | 3'UTR | 3 | 1716 | ccttcgagccaccacctggg | 42 | 70 |
| 150778 | 3'UTR | 3 | 1822 | cagtccaacctacccactgg | 5 | 71 |
| 150779 | 3'UTR | 3 | 1850 | ggattgcaagagtcaaaaag | 17 | 72 |
| 150780 | 3'UTR | 3 | 1860 | gtcagattgtggattgcaag | 20 | 73 |

TABLE 1-continued

Inhibition of human hematopoietic cell protein tyrosine kinase mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 150781 | 3'UTR | 3 | 1869 | cctgagaatgtcagattgtg | 24 | 74 |
| 150782 | 3'UTR | 3 | 1923 | gctgtaactaaaatccaacc | 10 | 75 |
| 150783 | 3'UTR | 3 | 1926 | acagctgtaactaaaatcca | 1 | 76 |
| 150784 | 3'UTR | 3 | 1954 | actattttgaaagtttccct | 10 | 77 |
| 150785 | 3'UTR | 3 | 1961 | tcatttcactattttgaaag | 0 | 78 |
| 150786 | 3'UTR | 3 | 1994 | taagacttgcatttatatct | 24 | 79 |
| 150787 | Intron 5 | 10 | 5506 | agatgtgcaccaccatgctt | 0 | 80 |
| 150788 | Intron 5 | 10 | 7370 | tgcaccaccctatattatca | 9 | 81 |
| 150789 | Intron 5 | 10 | 7447 | aacatacatattaggctggt | 0 | 82 |
| 150790 | Intron: Exon Junction | 10 | 8444 | gagtagcttcctgaattgac | 0 | 83 |
| 150791 | Intron: Exon Junction | 10 | 8941 | tcgttccctctggaacaga | 30 | 84 |
| 150792 | Exon: Intron Junction | 10 | 9094 | gggtccttacccatccagac | 6 | 85 |
| 150793 | Intron 9 | 10 | 17271 | ggccagcagaagatgccaca | 21 | 86 |
| 150794 | Intron: Exon Junction | 10 | 25867 | tttgacatccctgaaaagga | 22 | 87 |

As shown in Table 1, SEQ ID NOs 13, 17, 18, 19, 20, 22, 33, 34, 35, 36, 37, 39, 40, 42, 47, 51, 53, 57, 58, 66, 67, 68, 69, 70, 73, 74, 79, 84, 86 and 87 demonstrated at least 19% inhibition of human hematopoietic cell protein tyrosine kinase expression in this assay and are therefore preferred. The target sites to which these preferred sequences are complementary are herein referred to as "active sites" and are therefore preferred sites for targeting by compounds of the present invention.

Example 16
Western Blot Analysis of Hematopoietic Cell Protein Tyrosine Kinase Protein Levels Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to hematopoietic cell protein tyrosine kinase is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. An oligonucleotide 8 to 80 nucleobases in length targeted to nucleobases 67 through 144 of a 5'-untranslated region, nucleobases 258 through 1684 of a coding region, a stop codon region, or a 3'-untranslated region of a nucleic acid molecule of SEQ ID NO: 3 encoding hematopoietic cell protein tyrosine kinase, wherein said oligonucleotide specifically hybridizes with one of said regions and inhibits the expression of hematopoietic cell protein tyrosine kinase.

2. The oligonucleotide of claim 1 which is an antisense oligonucleotide.

3. The oligonucleotide of claim 2 wherein the antisense oligonucleotide comprises at least one modified internucleoside linkage.

4. The oligonucleotide of claim 3 wherein the modified internucleoside linkage is a phosphorothioate linkage.

5. The oligonucleotide of claim 2 wherein the antisense oligonucleotide comprises at least one modified sugar moiety.

6. The oligonucleotide of claim 5 wherein the modified sugar moiety is a 2'-o-methoxyethyl sugar moiety.

7. The oligonucleotide of claim 2 wherein the antisense oligonucleotide comprises at least one modified nucleobase.

8. The oligonucleotide of claim 7 wherein the modified nucleobase is a 5-methylcytosine.

9. The oligonucleotide of claim 2 wherein the antisense oligonucleotide is a chimeric oligonucleotide.

10. A composition comprising the oligonucleotide of claim 1 and a pharmaceutically acceptable carrier or diluent.

11. The composition of claim 10 further comprising a colloidal dispersion system.

12. The composition of claim 10 wherein the oligonucleotide is an antisense oligonucleotide.

13. A method of inhibiting the expression of hematopoietic cell protein tyrosine kinase in cells or tissues comprising contacting said cells or tissues in vitro with the oligonucleotide of claim 1 so that expression of hematopoietic cell protein tyrosine kinase is inhibited.

* * * * *